US006838040B2

(12) United States Patent
Mlinar et al.

(10) Patent No.: US 6,838,040 B2
(45) Date of Patent: Jan. 4, 2005

(54) METHOD FOR WEAKENING A PORTION OF A WEB

(75) Inventors: Joseph A. Mlinar, Appleton, WI (US); Todd W. Hajos, Greenville, WI (US); Kenneth J. Wagner, Greenville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 360 days.

(21) Appl. No.: 10/034,994

(22) Filed: Dec. 28, 2001

(65) Prior Publication Data

US 2003/0132549 A1 Jul. 17, 2003

(51) Int. Cl.[7] .......................... B29C 69/02; B29C 51/02; B29C 51/10; A61F 13/15

(52) U.S. Cl. ........................ 264/504; 264/555; 264/571; 264/154; 264/155; 264/156; 264/296; 425/290; 425/291; 425/305.1; 425/387.1; 425/388; 225/2; 225/96

(58) Field of Search ................................. 264/504, 555, 264/571, 154–156, 296; 425/290, 291, 305.1, 387.1, 388; 225/2, 96

(56) References Cited

U.S. PATENT DOCUMENTS

| | | | | |
|---|---|---|---|---|
| 3,488,778 A | | 1/1970 | Goujon et al. | 2/402 |
| 3,667,466 A | | 6/1972 | Ralph | 604/364 |
| 3,716,132 A | | 2/1973 | Lewyckyj | 428/43 |
| 3,835,754 A | * | 9/1974 | Lewyckyj | 493/346 |
| 3,845,682 A | | 11/1974 | Willhite et al. | 83/431 |
| 4,217,327 A | * | 8/1980 | Cancio et al. | 264/293 |
| 4,269,188 A | | 5/1981 | Nishizawa et al. | 604/368 |
| 4,407,284 A | | 10/1983 | Pieniak | 604/385.27 |
| 4,480,000 A | | 10/1984 | Watanabe et al. | 428/76 |
| 4,561,579 A | * | 12/1985 | Fleming et al. | 225/2 |

(List continued on next page.)

FOREIGN PATENT DOCUMENTS

| | | | | |
|---|---|---|---|---|
| DE | 198 13 334 A1 | | 9/1999 | A61F/13/15 |
| EP | 0319314 A2 | | 12/1988 | A61F/13/16 |
| EP | 0 570 980 A1 | | 11/1993 | A61F/13/15 |
| EP | 0844062 A1 | | 5/1998 | B29C/65/00 |
| EP | 0757550 B1 | | 12/1998 | A61F/13/56 |
| EP | 1 010 503 A2 | | 6/2000 | B26F/1/18 |
| EP | 0 907 510 B1 | | 3/2002 | B32B/31/18 |
| JP | 03176053 A | | 7/1991 | A61F/13/16 |
| JP | 3-205053 A | | 9/1991 | A61F/13/58 |
| JP | 10-315339 A | * | 12/1998 | B29C/70/06 |
| WO | WO 97/45333 A1 | | 12/1997 | B65D/75/28 |
| WO | WO 98/43573 A1 | | 10/1998 | A61F/13/15 |
| WO | WO 98/55292 A1 | | 12/1998 | B32B/7/04 |
| WO | WO 98/56328 A1 | | 12/1998 | A61F/13/15 |
| WO | WO 00/00119 A2 | | 1/2000 | A61F/13/00 |
| WO | WO 00 20208 A1 | | 4/2000 | B32B/27/02 |

OTHER PUBLICATIONS

Machine translation of JP 10–315339 A, 2004, Japanese Patent Office website.*

International Search Report for PCT/US02/20720, mailed on Sep. 23, 2002.

*Primary Examiner*—Leo B. Tentoni
*Assistant Examiner*—Michael I. Poe
(74) *Attorney, Agent, or Firm*—Brinks Hofer Gilson & Lione

(57) ABSTRACT

A method for weakening a portion of a web includes moving a web in a machine direction between at least a first location and a second location, wherein the second location is positioned downstream of the first location, forming a line of weakness in the web at the first location, wherein the web has a first tensile strength across the line of weakness, and weakening the line of weakness at a second location, wherein the web has a second tensile strength across the line of weakness after the line of weakness is weakened at the second location and wherein the first tensile strength is greater than the second tensile strength.

22 Claims, 7 Drawing Sheets

U.S. PATENT DOCUMENTS

| | | | | |
|---|---|---|---|---|
| 4,573,986 A | | 3/1986 | Minetola et al. | 604/366 |
| 4,610,681 A | | 9/1986 | Strohbeen et al. | 604/396 |
| 4,619,649 A | | 10/1986 | Roberts | 604/396 |
| 4,646,362 A | | 3/1987 | Heran et al. | 2/400 |
| 4,675,015 A | | 6/1987 | Brown | 604/385.09 |
| 4,681,580 A | | 7/1987 | Reising et al. | 604/385.3 |
| 4,687,477 A | | 8/1987 | Suzuki et al. | 604/385.25 |
| 4,699,622 A | | 10/1987 | Toussant et al. | 604/389 |
| 4,770,656 A | | 9/1988 | Proxmire et al. | 604/393 |
| 4,771,483 A | | 9/1988 | Hooreman et al. | 2/237 |
| 4,785,696 A | | 11/1988 | Martiny | 225/4 |
| 4,842,596 A | | 6/1989 | Kielpikowski et al. | 604/385.26 |
| 4,850,988 A | | 7/1989 | Aledo et al. | 604/385.21 |
| 4,850,992 A | | 7/1989 | Amaral et al. | 604/389 |
| 4,886,632 A | | 12/1989 | Van Iten et al. | 264/156 |
| 4,940,464 A | | 7/1990 | Van Gompel et al. | 604/396 |
| 4,946,086 A | | 8/1990 | Suuronen et al. | 83/152 |
| 5,037,414 A | | 8/1991 | Booth | 604/385.13 |
| 5,141,142 A | | 8/1992 | Ramsey | 225/4 |
| 5,340,424 A | | 8/1994 | Matsushita | 156/164 |
| 5,370,634 A | | 12/1994 | ANdo et al. | 604/385.21 |
| 5,375,751 A | | 12/1994 | Makinen | 225/1 |
| 5,415,649 A | | 5/1995 | Watanabe et al. | 604/385.29 |
| 5,449,353 A | | 9/1995 | Watanabe et al. | 604/385.27 |
| 5,531,732 A | | 7/1996 | Wood | 604/391 |
| 5,562,964 A | * | 10/1996 | Jones | 428/43 |
| 5,573,524 A | | 11/1996 | Sardo | 604/385.16 |
| 5,603,708 A | | 2/1997 | Seth | 604/389 |
| 5,704,566 A | * | 1/1998 | Schutz et al. | 242/595 |
| 5,746,730 A | | 5/1998 | Suzuki et al. | 604/385.26 |
| 5,795,350 A | | 8/1998 | Schmitz | 604/391 |
| 5,820,617 A | | 10/1998 | Igaue et al. | 604/385.25 |
| 5,855,574 A | | 1/1999 | Kling et al. | 604/392 |
| 5,858,515 A | | 1/1999 | Stokes et al. | 428/195.1 |
| 5,876,392 A | | 3/1999 | Hisada | 604/385.29 |
| 5,879,500 A | | 3/1999 | Herrin et al. | 156/204 |
| 5,881,622 A | | 3/1999 | Kaipf | 83/349 |
| 6,027,484 A | | 2/2000 | Romare | 604/386 |
| 6,033,353 A | | 3/2000 | Lencoski et al. | 493/352 |
| 6,083,210 A | | 7/2000 | Young et al. | 604/367 |
| 6,110,157 A | | 8/2000 | Schmidt | 604/385.01 |
| 6,132,410 A | | 10/2000 | Van Gompel et al. | 604/385.25 |
| 6,160,200 A | | 12/2000 | Ehrnsperger et al. | 604/378 |
| 6,217,563 B1 | | 4/2001 | Van Gompel et al. | 604/385.101 |
| 6,264,641 B1 | | 7/2001 | Van Gompel et al. | 604/385.22 |
| 6,336,922 B1 | | 1/2002 | Van Gompel et al. | 604/385.3 |
| 6,361,527 B1 | | 3/2002 | Van Gompel et al. | 604/385.25 |
| 6,368,689 B1 | * | 4/2002 | Connor Sledge et al. | 428/43 |
| 6,375,646 B1 | | 4/2002 | Widlund et al. | 604/385.3 |
| 6,395,211 B1 | * | 5/2002 | Dettmer et al. | 264/156 |
| 6,478,786 B1 | | 11/2002 | Glaug et al. | 604/385.27 |

* cited by examiner

METHOD FOR WEAKENING A PORTION OF A WEB

BACKGROUND

The present invention relates to a method and apparatus for weakening a portion of a web.

Many types of consumer goods are produced with a weakened region, such as a perforation, that allows a user to separate one portion of the good from another. For example, paper towels and toilet paper are typically provided with perforations that allow the user to separate one or more towels or sheets of tissue from a roll thereof. Likewise, many types of paper forms and computer paper have continuous webs of material that can be separated into one or more distinct, separate pages by breaking a weakened region thereof, for example a perforation. Similarly, plastic wrap and bags often are provided with perforations allowing the wrap to be torn, or a bag to be separated from a roll of such bags.

Typically, the types of consumer goods mentioned above are manufactured on a continuous basis on large scale manufacturing lines. Usually, various raw products or components are formed on, or integrated into, a continuous stream of material, which often includes a web of material that moves in a machine direction through and along the line. As such, it is important to maintain the integrity of the stream of material or web and minimize breaks thereof during the process so as to avoid costly downtime. In general, however, the web is pushed or pulled along the line, so as to put the web in tension. Accordingly, the formation of regions of weakness, especially along a cross-direction, can increase the risk of breakage. Therefore, it is desirable to maximize the tensile strength of the stream of materials or web as it passes through the process. At the same time, it is desirable for the end user to be able to break the various regions of weakness without undue effort, especially for people with reduced hand strength or dexterity, as can be caused, for example, by arthritis. Accordingly, there remains a need for maximizing the tensile capabilities of a stream of material or web across a weakened region during the processing of the consumer good, but also for minimizing the tensile capabilities across that same weakened region in the end product.

In other situations, the stream of material or web is weakened and then broken downstream, for example by accelerating the web on one side of the weakened region, often near the end of the process where the discrete products or goods are then acted on individually. Such methods and apparatus, however, typically require complex and expensive components to effect the timely acceleration and deceleration of the web. Accordingly, there also remains a need to provide a simple and effective way to break a web at a weakened region.

SUMMARY

Briefly stated, in one preferred embodiment, a method for weakening a portion of a web includes moving a web in a machine direction between at least a first location and a second location, wherein the second location is positioned downstream of the first location. In one preferred embodiment, the method further includes forming a line of weakness in the web at the first location, wherein the web has a first tensile strength across the line of weakness. Preferably, the method also includes weakening the line of weakness at a second location, wherein the web has a second tensile strength across the line of weakness after the line of weakness is weakened at the second location and wherein the first tensile strength is greater than the second tensile strength.

In one preferred embodiment of the invention, the method includes forming a cross-direction line of weakness in the web. Also in one preferred embodiment, the first line of weakness is formed at the first location by perforating the web.

In another aspect, one preferred embodiment of a method includes moving a web through a nip, wherein the nip is defined by first and second moveable members. The first moveable member comprises at least one insert member and the second moveable member comprises at least one recess shaped to receive the insert member. Preferably, the method includes pushing at least a portion of the web at the line of weakness with the insert member into the recess.

In another aspect, one preferred embodiment of an apparatus for weakening a portion of a web includes a first roll having a first outer surface and an insert member extending outwardly from the first outer surface. The first roll rotates about a first longitudinal axis. The apparatus also preferably includes a second roll having a second outer surface and a recess extending inwardly from the second outer surface. Preferably, the second roll rotates about a second longitudinal axis and the first and second outer surfaces form a nip therebetween. Preferably, the insert member is received in the recess at the nip.

In another aspect, an absorbent garment is configured with a line of weakness that permits a user to break one or more portions thereof so as to remove the garment, or so as to allow it to be expanded to fit the user. For example, the absorbent garment can be configured as a pant-type, pull-on garment with a refastenable fastening system. In use, the user may break the garment along a line of weakness to adjust the fit of the garment and thereafter rely on the refastenable fastening system to retain the garment on the user. Alternatively, the user can break the line of weakness and apply the garment as a diaper-type garment, which is drawn up between the legs of the user and secured to the user with the fastening system. Preferably, the line of weakness has sufficiently low tensile and tear strengths at the line of weakness such that the user can easily break the garment at the line of weakness.

The various preferred embodiments provide significant advantages over other methods and apparatuses for weakening a portion of a web. For example, the stream of material or web can be provided with a line of weakness at the first location having a sufficiently high tensile strength that allows the stream or web to be pushed or pulled through the process without breaking. When it is desirable to weaken the line of weakness, for example near the end of the process where a sustained tensile strength is less important or where fastener members have been applied across the line of weakness so as reinforce the web at that location, the line of weakness can be further weakened, such that a user can more easily break the line of weakness when desired. The process also can be used to completely break the line of weakness, for example to form discrete products.

The apparatus also provides a simple, but effective device for weakening the line of weakness. In particular, the apparatus avoids the need to accelerate the stream or web, or to otherwise change the draw of the machine. Moreover, the insert member, or members, can be easily switched and interchanged to provide more or less weakening of the line of weakness, for example, by altering the shape and/or size of the insert member.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of the web thicknesses and the like, may be somewhat exaggerated for the sake of illustration and clarity.

DETAILED DESCRIPTION OF THE PRESENTLY PREFERRED EMBODIMENTS

Figure 16:
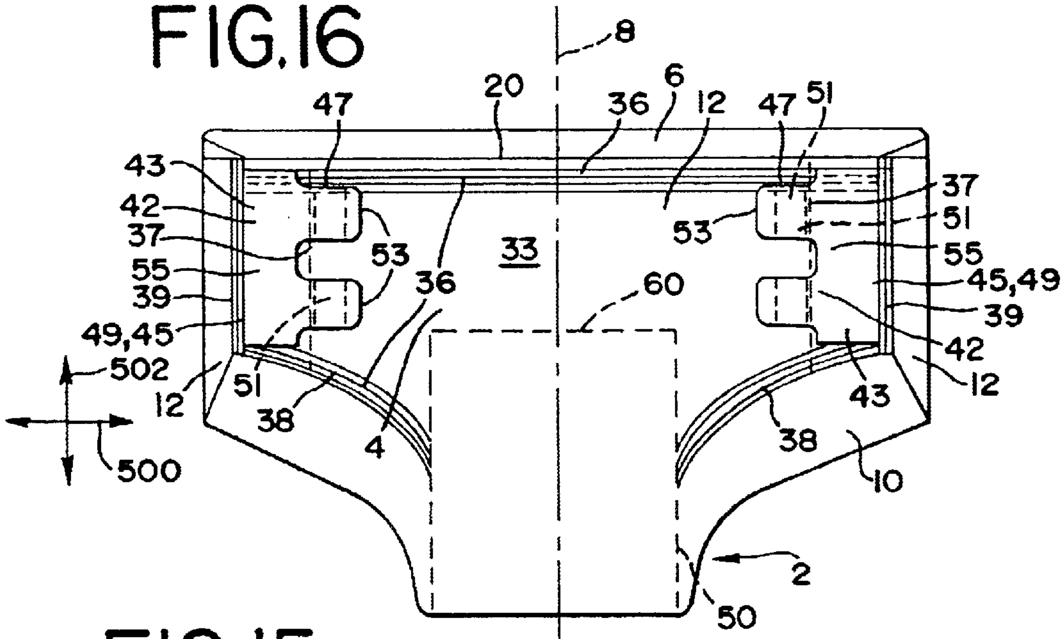
FIG. 16 is a front perspective view of one preferred embodiment of an absorbent garment in a folded configuration.
Figure 15:
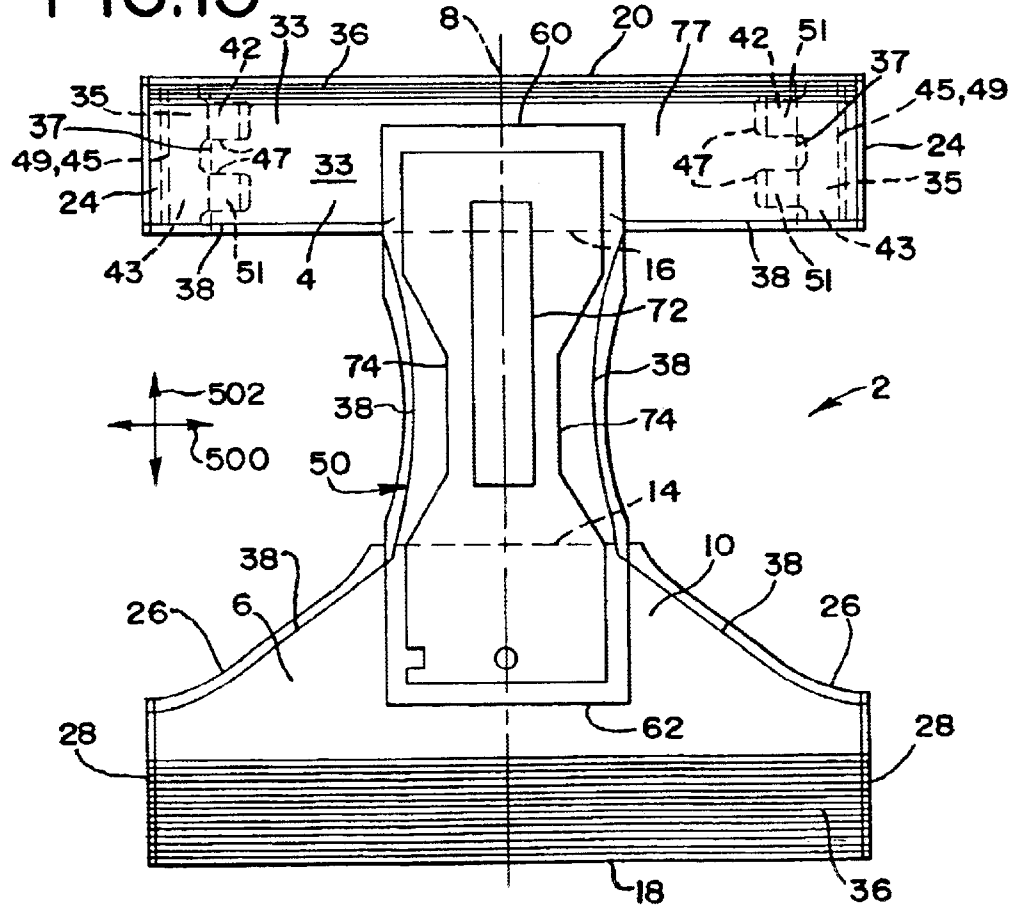
FIG. 15 is a plan view of one preferred embodiment of an absorbent garment in an unfolded configuration.

Definitions:

Referring to FIGS. 15 and 16, it should be understood that the term "longitudinal," as used herein, means of or relating to length or the lengthwise direction 502, and in particular, the direction running between the front and back of the user. The term "laterally," as used herein means situated on, directed toward or running from side to side, and in particular, a direction 500 running from the left to the right of a user, and vice versa. The terms "upper," "lower," "inner," and "outer" as used herein are intended to indicate the direction relative to the user wearing an absorbent garment over the crotch region, while the terms "inboard" and "outboard" refer to the directions relative to a centerline 8 of the garment. For example, the terms "inner" and "upper" refer to a "body side," which means the side closest to the body of the user, while the terms "outer" and "lower" refer to a "garment side."

The term "body side" should not be interpreted to mean in contact with the body of the user, but rather simply means the side that would face toward the body of the user when the garment is applied to the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user when the garment is applied to the user, and therefore toward any outer garments that may be worn by the user, regardless of whether the absorbent garment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, one web may be traveling along a first machine direction, which is substantially perpendicular to the travel of another web in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, or of one or more connected in-line pieces, and regardless of whether it may have non-continuous, discrete items disposed thereon, or is made up of connected non-continuous, discrete items. For example, and without limitation, a web includes various paper products, tissue, including toilet paper and facial tissue, paper towels, cardboard, plastic, such as plastic wraps or bags, films, various components and assemblies of absorbent garments, including for example body panels, etc., which may be comprised of nonwoven materials, such as spunbond materials, woven materials, multi-directional elastic materials, and various combinations thereof.

The term "weakening" means to cause to lose strength, such that the area that is weakened is not as strong as the adjacent areas. For example, and without limitation, an area that is weakened may have a lesser tear or tensile strength as compared with the adjacent areas of the web, such that the web is more likely to be torn or broken along the area of weakness rather than the adjacent areas. In this way, the manufacturer can control the area of the web that will be broken, whether such breakage is performed by the end user or at a later time during the manufacturing or fabrication process.

The term "line of weakness" refers to any region or area of weakened material, preferably having a length and which may or may not have a defined width, and can include linear and non-linear patterns, such as curvilinear patterns of weakness, or other shapes, such as a circles, rectangles, etc. The line of weakness can include a perforation or other series of cuts, a thinning, or breakage or separation of material, or a strip of a different kind of material bridging between adjacent portions of material, that is more easily torn or broken than the adjacent portions, and which allow the user or manufacturer to separate the adjacent portions along the line of weakness.

Figure 1:
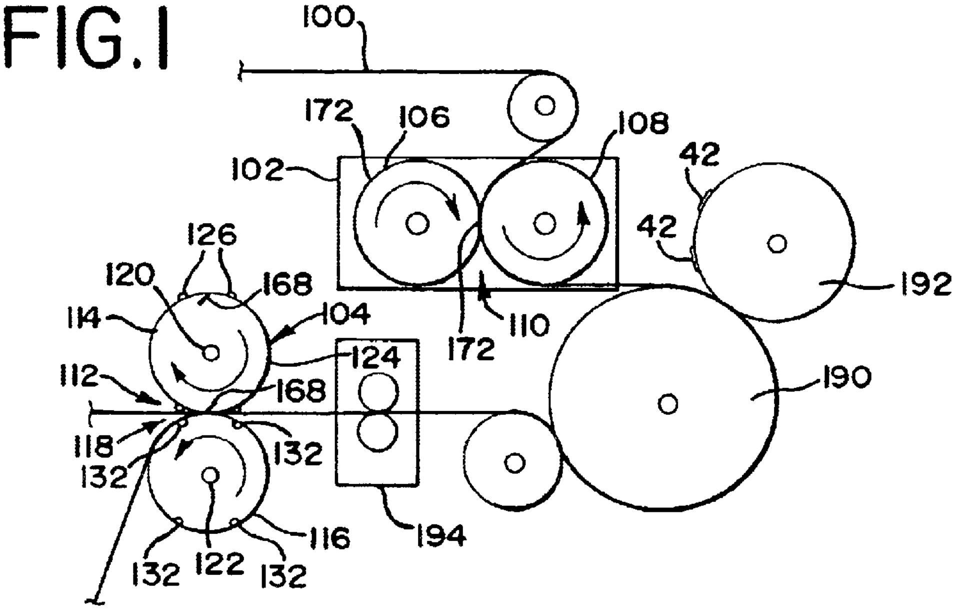
FIG. 1 is a schematic representation of a method and apparatus for weakening a portion of a web.

Method and Apparatus:

Referring to FIG. 1, a web 100 is shown as moving in a machine direction along a process line. The web 100 is passed through a first weakening apparatus 102 at a first location 110 and through a second weakening apparatus 104 at a second location 112 positioned downstream of the first location 110. The first weakening apparatus 102 forms a line of weakness 37 in the web 100, as shown for example in FIG. 14. In a preferred embodiment, the first weakening apparatus 102 forms a cross-direction line of weakness 37, which is preferably linear, in the web. The line of weakness can extend across the entire cross-direction width of the web, or along only a portion thereof.

Referring again to FIG. 1, in one preferred embodiment, the first weakening apparatus 102 is configured as a perforator having a knife roll 106 and an anvil roll 108. Alternatively, the weakening apparatus can be configured with a laser, water jet, or other types of cutters known in the art. In other alternative embodiments, the weakening apparatus can comprise a device for applying heat, thermal energy or ultrasonic energy to the web so as to weaken it at specific locations, or lines of weakness. In other preferred embodiments, the weakening apparatus can include a chemical applicator that applies various chemicals, including for example water, to the web to weaken it at specific locations. In yet another alternative embodiment, the apparatus applies a speed differential to the web so as to weaken the web. Of course, it should be understood that the weakening apparatus can also be configured from combinations of one or more of the above-referenced devices.

As the web 100 leaves the first weakening apparatus 102 at the first location 110, the web preferably has a first tensile strength and a first tear strength measured across and along the line of weakness 37 respectively, as explained below. For example, with respect to absorbent garment body panels, it is generally desired to maintain a mean tensile strength of a body panel web, measured along the entire cross-direction length of the web (e.g., 6.37 inches (162 mm) in one preferred embodiment) and across the line of weakness, between about 0.90 kg (8.83 N or 1.99 lbf) to about 8.60 kg (84.37 N or 18.97 lbf) to run the web through the manufacturing process. As referred to and used herein, the tensile and tear strength values are mean or average values for a group of at least 20 samples.

Figure 2:
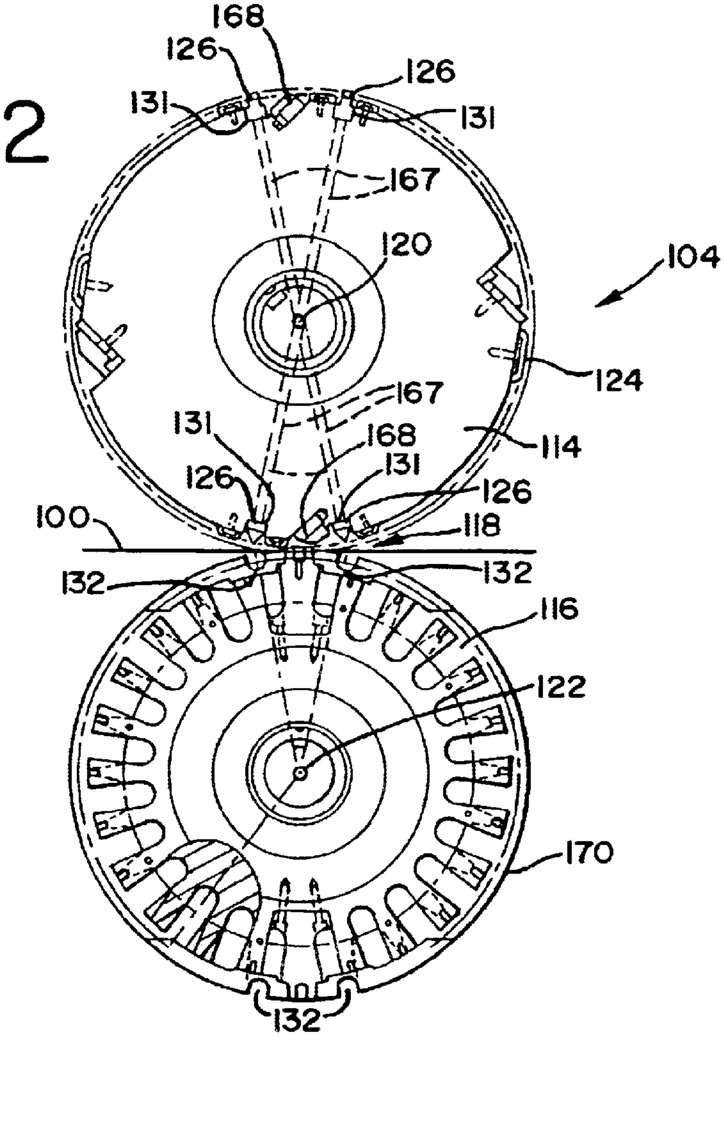
FIG. 2 is a side view of a web weakening apparatus.

Referring to FIGS. 1 and 2, the second weakening apparatus 104 can be configured from any of the above-referenced devices. The second weakening apparatus 104 weakens the web 100 at the line of weakness 37. For example, with respect to absorbent garment body panels, it is generally desired to maintain a mean tensile strength across the line of weakness of between about 0 kg to about 6.30 kg (61.8 N or 13.9 lbf), or preferably less than 14 lbf, for the end user, or more preferably between about 0 kg and about 3.00 kg (29.43 N or 6.62 lbf), or preferably less than 7 lbf, or alternatively preferably less than about 22.24 N or 5 lbf, or alternatively preferably less than about 1.36 kg (13.35 N or 3 lbf), wherein the tensile strength of the body panels across the line of weakness is determined using the testing protocol described below from a group of at least 20 samples. Likewise, with respect to absorbent garment body panels, it is generally desired to maintain a mean trapezoidal tear strength along the line of weakness of between about 0 kg to about 2.27 kg (22.25 N or 5 lbf), for the end user, and more preferably between about 0 kg and about 1.82 kg (17.84 N or 4 lbf), and more preferably less than about 1.36 kg (13.35 N or 3 lbf), wherein the tear strength of the body panels along the line of weakness is determined, and samples obtained, using the testing protocol described below from a group of at least 20 samples.

In particular, as the web leaves the second weakening apparatus, the web 100 has a second tensile strength and a second tear strength measured across the line of weakness, which are less than the first tensile strength and first tear strength respectively. It should be understood that, for the purpose of simply determining the difference between the tensile and tear strengths measured across and along the line of weakness after the web passes the first and second locations, any testing protocol can be used, so long as the samples and protocol used to test the web after it passes each location are the same for comparison purposes. However, when it is desired to determine specific values of the tear and tensile strength of the web after it passes the second location, and more preferably the tear and tensile strengths of the web, or component formed from the web, as it will be used by the end user, for example and without limitation an absorbent garment body panel, the samples and values should be prepared and obtained, respectively, in accordance with the testing protocol set forth herein below, with the tear and tensile strengths of the web or component being calculated as mean or average values from a group of at least 20 samples.

Preferably, the second tensile and tear strengths are greater than zero, such that the web remains intact until it is completely severed at the line of weakness, or at another location on the web, as explained below, so as to form discrete articles. However, it should be understood that the second weakening apparatus can completely sever the web at the line of weakness. In addition, it should be understood that the two weakening apparatus, and two locations, are meant to be illustrative rather than limiting, and that additional weakening apparatus and locations can be used to further weaken the web at a line of weakness downstream from the first and second locations.

In one preferred embodiment, shown in FIGS. 1, 2, 12 and 13, the second weakening apparatus 104 includes first and second moveable members or rolls 114, 116 forming a nip 118 through which the web passes. The first roll 114 is preferably configured as a knife roll, with the second roll 116 preferably configured as an anvil roll. The first and second rolls 114, 116 rotate in opposite directions about first and second longitudinal axes 120, 122 respectively. The first roll 114 has an outer surface 124 and a plurality of insert members 126 extending outwardly from the outer surface, and preferably extending radially outward from the outer surface. In a preferred configuration, the first roll 114 includes two pairs of circumferentially spaced insert members 126, with the pairs being circumferentially spaced around the periphery of the roll about 180 degrees at opposite perimeter positions. It should be understood that the positions of the insert members 126 can be spaced at any location around the perimeter or periphery of the roll, and moreover that the two pairs are meant to be illustrative rather than limiting. Preferably, a plurality, meaning two or more, insert members are spaced around the periphery of the roll. Preferably, the insert members 126 are positioned so as to be indexed with the lines of weakness 37 formed in the web by the first weakening apparatus 102 as the lines of weakness are passing through the nip 118. Preferably, the insert members 126 have a length extending along a cross-direction parallel to the longitudinal axis 120 of the roll 114.

Referring to FIGS. 3–9B, various exemplary configurations of the insert member are shown. Preferably, the insert members 126, as shown in FIGS. 4–9B include a base 128 and a plurality of, meaning two or more, longitudinally spaced insert portions 130 extending therefrom. The base 128 is received in a recess 131 formed radially inward from the outer surface of the roll 114, with the insert portions 130 extending preferably radially outwardly past the outer surface. The base 128 can be mounted to the roll 114 with fasteners extending through openings 134, or by welding, bonding or other known attachment devices. The insert members 126 are preferably made of hard plastic, metal, fiberglass or other suitably rigid materials.

In one preferred embodiment, the insert portions 130 are spaced apart, such that the line of weakness 37, preferably formed as a perforation, is weakened only at those locations, with the line of weakness 37 substantially retaining its original strength as imparted after the first weakening apparatus at the spaces 136 or the locations between the insert portions. For example, in one preferred embodiment, the insert members 126 are shown as having three insert portions 130 with two spaces 136 formed therebetween. In one preferred embodiment, the insert portions 130 are spaced so as to weaken the line of weakness between tab members 53 of a fastener member 42 that bridges the line of weakness. Of course, it should be understood that the insert member could be configured with a single insert portion, two insert portions or four or more insert portions.

Figure 3:
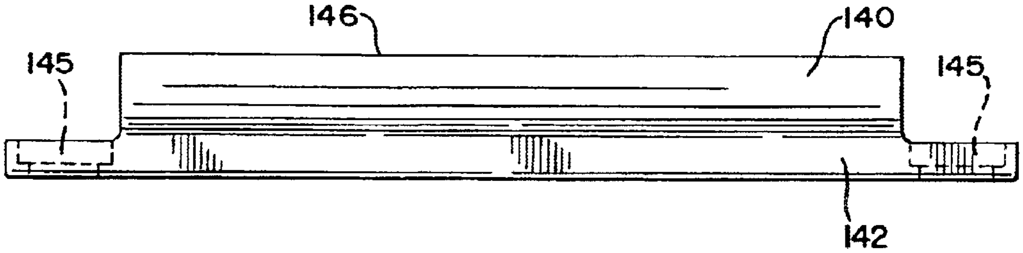
FIG. 3 is a front view of a first preferred embodiment of an insert member.
Figure 3A:
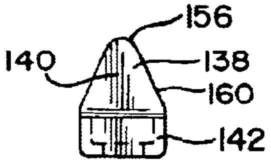
FIG. 3A is a side end view of the insert member shown in FIG. 3.
Figure 3B:
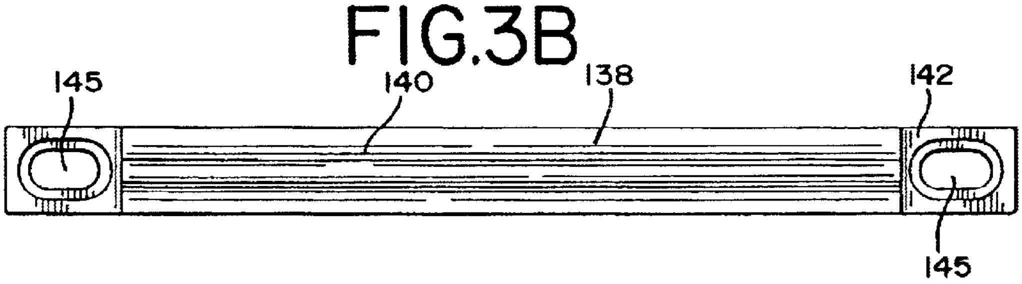
FIG. 3B is a top view of the insert member shown in FIG. 3.

For example, in one preferred embodiment, shown in FIGS. 3–3B, the insert member is configured as an elongated bar 138 having a continuous insert portion 140 and a base portion 142 that can be secured to the roll 114 in the recess 131 inwardly from the surface 114, for example with fasteners passing through the base portion thereof at openings 145, which are preferably include counter sinks. Preferably, the insert portion 140 has the same or greater length than the length of the line of weakness and therefore functions to weaken the entire line of weakness 37. It should be understood that in an alternative embodiment, the insert member can be configured simply as a flat bar having an edge that extends beyond the outer surface of the roll.

Figures 4, 4A, 4B, 5, 5A, 5B, 6, 6A, 6B, 7, 7A, 7B, 8, 8A, 8B, 9, 9A, 9B:
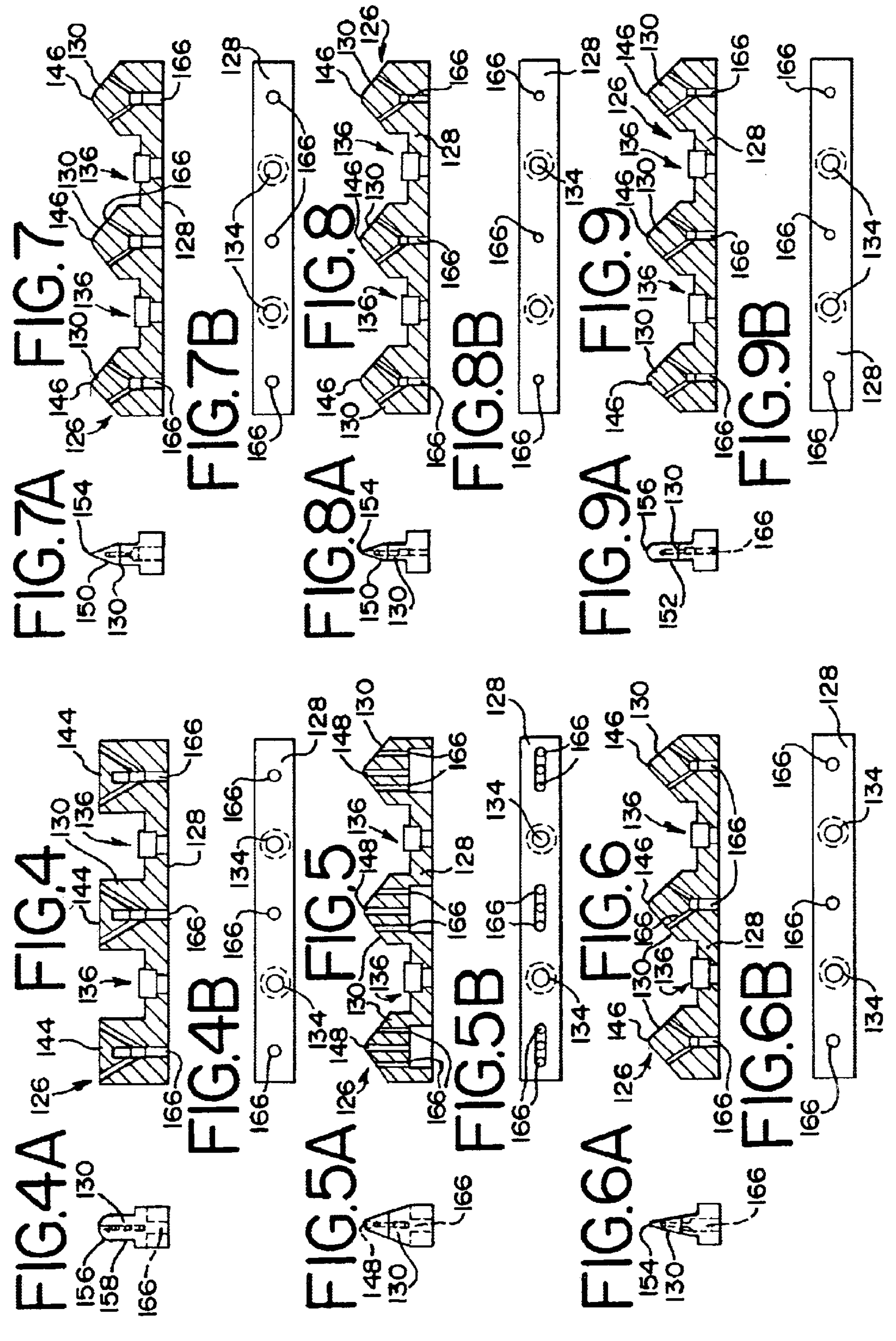
FIG. 4 is a front view of a second preferred embodiment of an insert member.
FIG. 4A is a side end view of the insert member shown in FIG. 4.
FIG. 4B is a bottom view of the insert member shown in FIG. 4.
FIG. 5 is a front view of a third preferred embodiment of an insert member.
FIG. 5A is a side end view of the insert member shown in FIG. 5.
FIG. 5B is a bottom view of the insert member shown in FIG. 5.
FIG. 6 is a front view of a fourth preferred embodiment of an insert member.
FIG. 6A is a side end view of the insert member shown in FIG. 6.
FIG. 6B is a bottom view of the insert member shown in FIG. 6.
FIG. 7 is a front view of a fifth preferred embodiment of an insert member.
FIG. 7A is a side end view of the insert member shown in FIG. 7.
FIG. 7B is a bottom view of the insert member shown in FIG. 7.
FIG. 8 is a front view of a sixth preferred embodiment of an insert member.
FIG. 8A is a side end view of the insert member shown in FIG. 8.
FIG. 8B is a bottom view of the insert member shown in FIG. 8.
FIG. 9 is a front view of a seventh preferred embodiment of an insert member.
FIG. 9A is a side end view of the insert member shown in FIG. 9.
FIG. 9B is a bottom view of the insert member shown in FIG. 9.

Referring to the embodiments of FIGS. 3–9B, the insert portions 130, 140 can be configured with different top and side profiles. For example, as shown in FIG. 4, the insert portion 130 can have a relatively flat upper or outermost surface 144 or edge. Alternatively, as shown in FIGS. 3–3A and 5–9A, the outermost surface can be tapered to facilitate entry into the line of weakness, or perforation hole formed in the web. The apex or noses 146, 148 of the top surface can be relative rounded, as shown in FIGS. 6, 7, 8 and 9, or sharp as shown in FIG. 5. The insert portions 130 also can be relatively thin, as shown in FIGS. 7A, 8A and 9A, with tapered sides 150 forming a sharp apex 154 (FIGS. 7A and 8A) or flat sides 152 with a rounded nose 156 (FIG. 9A). Alternatively, the insert portions can have a greater thickness, as shown in FIGS. 4A, 5A and 6A, with flat sides 158 and a rounded nose 164 (FIG. 4A), or tapered sides 160 and a sharp nose 162 (FIG. 6A), or some combination thereof (FIGS. 3A and 5A).

In one preferred embodiment, shown in FIGS. 4–9B, the insert portions are configured with one or more channels 166 formed therein. An air supply, preferably a positive pressure (although a vacuum also could be applied), is applied to the web 100 through the channels 166. Preferably, the channels form a plurality of, and preferably two, exit ports on the upper surface of the insert portion. As shown in FIG. 2, an input port of the channels 166 communicate with a channel 167 or other air supply formed in the first roll 114.

In one preferred embodiment, shown in FIGS. 1 and 2, the first roll 114 further includes a pair of knives 168 mounted to the roll between the pairs of insert members 126 on opposite sides of the roll. It should be understood that more knives, and/or insert members, can be positioned around the circumference of the roll as needed.

Referring to FIGS. 1, 2, 12 and 13, the second roll 116 has an outer surface 170 and a plurality of recesses 132 formed and extending inwardly from the outer surface. Preferably, the recesses 132 extend radially inward from the outer surface and are circumferentially spaced so as to mate with and receive the insert portions 130, 140 of the first roll at the nip 118 formed between the two rolls, as shown for example in FIG. 13. In addition, the recesses 132 are preferably formed along the cross-direction in the longitudinal direction and have a length dimensioned to receive the insert members 126, and in particular the insert portions 130, 140 thereof.

In one preferred embodiment, the two rolls 114, 116 cooperate to weaken the line of weakness 37 as at least a portion of the web 100 is forced by the insert portions 130, 140 into the recesses 132 formed in the second roll so as to separate portions of the web along the line of weakness or to enlarge or unite the various perforation openings formed by the first weakening apparatus.

Also in one preferred embodiment, the knife 168 engages an outer surface of the anvil roll 116 so as to completely sever the web at a location between the proximate lines of weakness making up each pair of lines of weakness. In this way, various discrete products, such as absorbent garments, are formed, each having a line of weakness.

Figure 10:
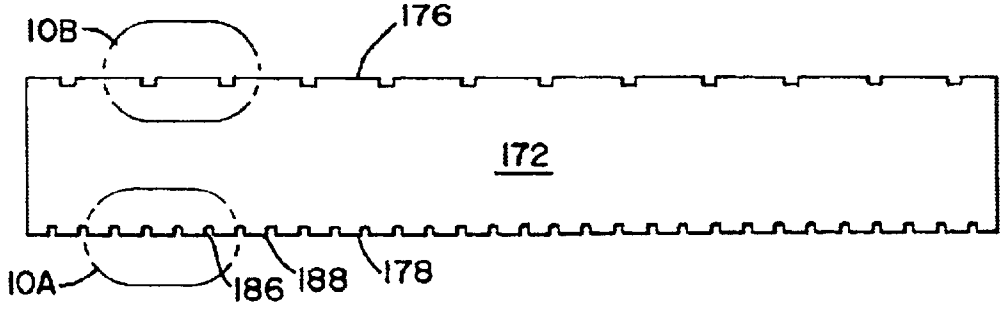
FIG. 10 is a front view of one preferred embodiment of a perforation knife.
Figure 10B:
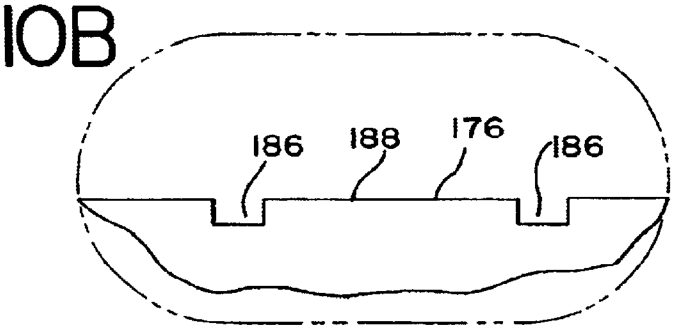
FIG. 10B is an enlarged partial view of a portion of the perforation knife embodiment taken along the area 10A of FIG. 10.
Figure 10A:
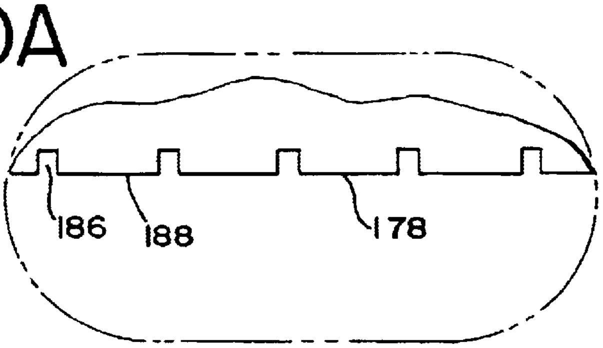
FIG. 10A is an enlarged partial view of a portion of the perforation knife embodiment taken along the area 10A of FIG. 10.
Figure 11:
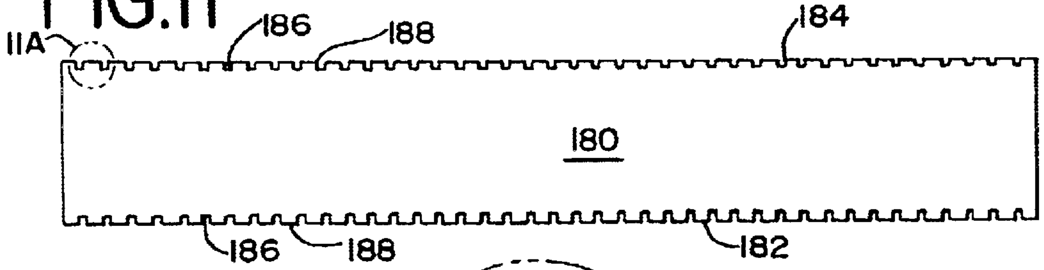
FIG. 11 is a front view of another preferred embodiment of a perforation knife.
Figure 11A:
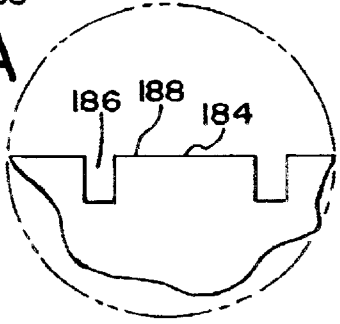
FIG. 11A is an enlarged partial view of a portion of the perforation knife embodiment taken along the area 11A of FIG. 11.
Figure 12:
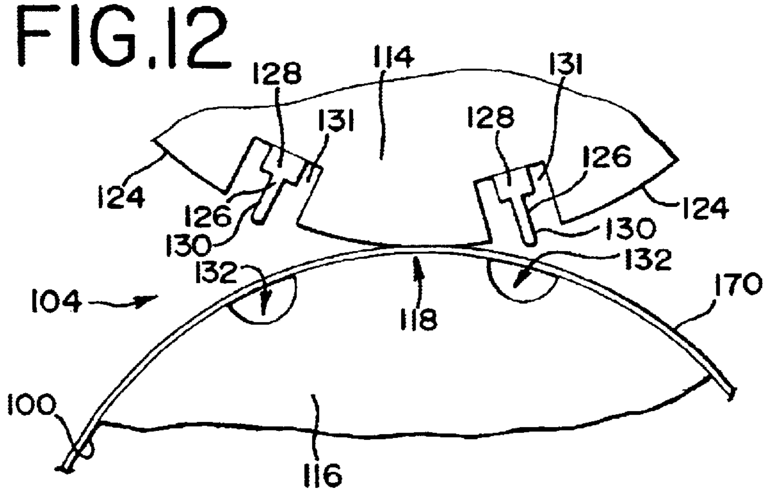
FIG. 12 is an enlarged view of a portion of a weakening apparatus at a nip.
Figure 13:
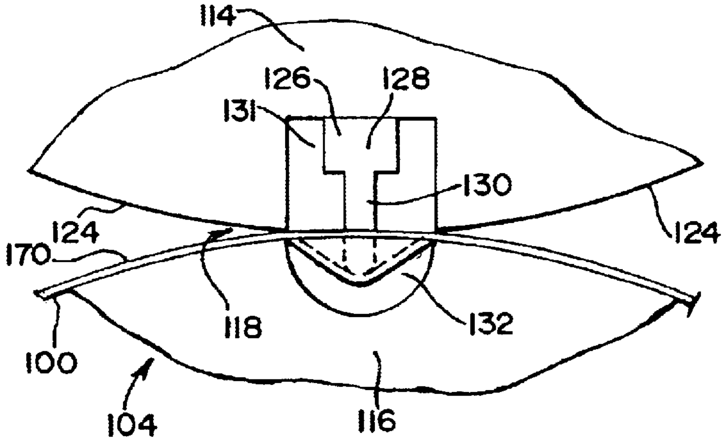
FIG. 13 is an enlarged view of a portion of a weakening apparatus at a nip.

In one preferred alternative embodiment, the web 100 is weakened only at one location. For example, the web can be weakened near the end of the process where the risk of breakage is reduced. Alternatively, in one preferred embodiment, as explained below, fastener members 42 can be applied over and bridge the line of weakness to maintain the integrity of the web as it travels through the process. Referring to FIGS. 1 and 10–11A, the web 100 is preferably weakened to a level wherein a user can easily tear and/or break the web without undue effort, as explained herein. In one preferred embodiment, the line of weakness is formed using a knife 172 and an anvil, preferably using a knife roll 106 and an anvil roll 108. Various preferred embodiments of the knife 172 are shown in FIGS. 10–11A. In the embodiment of FIG. 10, the knife 172 is formed with a first and second edge 176, 178, each having a different pattern of notches 186 and cutting edges 188. The cutting edges 188 severs a portion of the web 100 and forms an opening, with the notch 186 forming a landing portion between the openings, thereby defining a perforation or line of weakness 37 in the web, with the perforation made up of alternating landings and openings. The cutting edges also can be configured to cut, partially or completely, any elastic elements that may be formed in the web. Indeed, if the notch is shallow enough, e.g., about 0.050 inches, the elastic element can be nicked or partially severed even if it falls in the notch, thereby further weakening the web. The knife 172 can be flipped or rotated to present one or the other of the first and second edges 176, 178 to the anvil roll 108. In this way, a single knife can be used to provide two different perforation patterns.

Alternatively, as shown in FIG. 11, the knife 180 is configured with the same pattern on each edge 182, 184 of the knife. In this instance, the knife 180 can be flipped or rotated once one edge becomes dull, without altering the pattern that will be imparted to the web. Of course, it should be understood that a knife could be configured with notches along only one edge thereof.

In any of the embodiments, at least one knife edge 176, 178, 182, 184 is provided with a plurality of spaced notches 186 that define and form a plurality of spaced cutting edges 188 that are presented to the anvil. The width of the notches and cutting edges can be altered to provide a greater or lesser amount of cut material and a corresponding greater or lesser weakening of the web. In addition, the knife edge can be made with varying thicknesses which define the width of the opening, or can be formed as a die cutter, with the cutting edges having one or more various cross-sections, including without limitation a diamond cut, a round cut, etc. Preferably, the knife 172, 180 has a length equal to or greater than the length of the line of weakness. The knives are preferably made of tool steel, although other materials would also work.

In one preferred embodiment, the perforation knife is about 9 inches (22.86 cm) long and has between about 10 and 75 notches spaced therealong. The notches are preferably between about 0.050 and 0.075 inches (1.27–1.91 mm) deep, and more preferably about 0.063 inches (1.6 mm) deep. The notches also are preferably between about 0.005 and about 0.12 inches (0.127–3.05 mm) wide. The cutting edges formed between the notches are preferably between about 0.10 inches (2.54 mm) and about 0.65 inches (16.51 mm). In one preferred embodiment, the cutting edge is less than 0.256 inches (6.50 mm), and more preferably less than 0.236 inches (6.00 mm), and the notch width is preferably less than 0.059 inches (1.50 mm). Various preferred embodiments for the knife blade are listed below in Table 1.

TABLE 1

Perforation Knife Configurations

| Embodiment | Notch Width (in/mm) | Cutting Edge Width (in/mm) |
|---|---|---|
| 1 | 0.0394/1 | 0.1771/4.5 |
| 2 | 0.0492/1.25 | 0.2461/6.25 |
| 3 | 0.0394/1 | 0.2165/5.5 |
| 4 | 0.0591/1.5 | 0.246/6.25 |
| 5 | 0.0177/.45 | 0.2067/5.25 |
| 6 | 0.0138/.25 | 0.2067/5.25 |
| 7 | 0.0256/.65 | 0.2067/5.25 |
| 8 | 0.0217/.55 | 0.2067/5.25 |
| 9 | 0.005/.127 | 0.183/4.636 |
| 10 | 0.005/.127 | 0.12/3.05 |
| 11 | 0.0295/.75 | 0.27067/5.25 |
| 12 | 0.005/.127 | 0.200/6.223 |
| 13 | 0.0591/1.50 | 0.196/5.00 |

Figure 14:
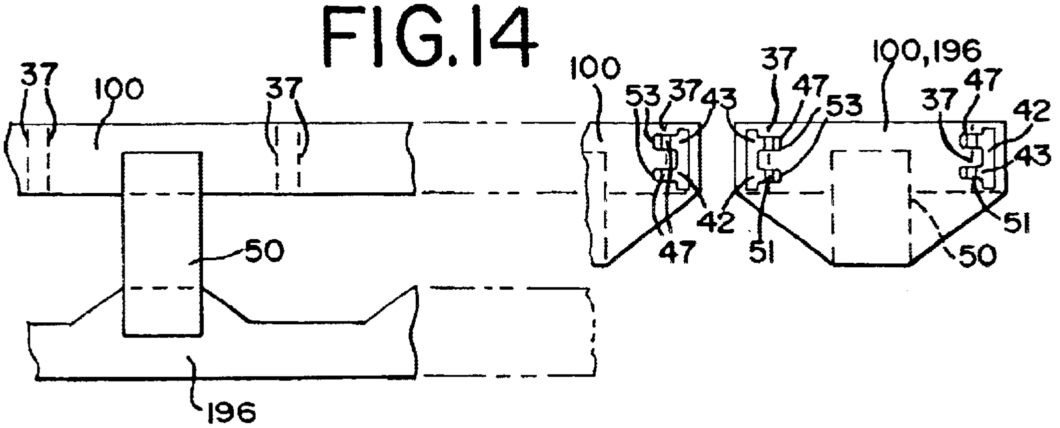
FIG. 14 is a schematic representation of a method of making an absorbent garment.

Referring to FIGS. 1 and 14, one preferred method of weakening a portion of a web is in the context of weakening a portion of a body panel incorporated into an absorbent garment. However, it should be understood that the web can be configured as paper towels, various paper products, tissue, cardboard, plastic, etc. In one preferred embodiment, a body panel web 100 passes through the first weakening apparatus 102 and around a construction drum 190. Preferably the first weakening apparatus 102 successively forms pairs of cross-direction lines of weakness 37 in the body panel web, where the lines within each pair and successive pairs of lines of weakness are spaced in the longitudinal direction. Various fastener members 42 are applied to the web over the lines of weaknesses 37 on the construction drum using a fastener applicator 192. The fastener applicator can be configured as an offset cam action rotator, which rotator and the method for the use thereof, is further disclosed in U.S. Pat. Nos. 5,761,478, 5,759,340, and 6,139,004, all of which are assigned to Kimberly-Clark Worldwide, Inc., the assignee of the present application, the entire disclosures of all of which are hereby incorporated herein by reference. Alternatively, the subassembly can be rotated using a revolving transfer roll as shown and described in U.S. Pat. No. 4,608,115, which is assigned to Kimberly-Clark Worldwide, Inc., the assignee of the present application, and which is hereby incorporated herein by reference in its entirety.

Preferably, the fastener members 42 have tabs 53 spaced along the cross direction that cross or bridge the lines of weakness 37. The fastener members, which are applied soon after the lines of weakness are formed, maintain the integrity of the web as it continues through the process.

Various methods and apparatus for manufacturing absorbent garments and for applying fastener members thereto are disclosed in U.S. patent application Ser. No. 09/954,506, filed Sep. 14, 2001, and entitled Method and Apparatus For Assembling Refastenable Absorbent Garments, U.S. patent application Ser. No. 09/954,444, filed Sep. 14, 2001, and entitled Method and Apparatus For Assembling Refastenable Absorbent Garments, U.S. patent application Ser. No. 09/954,478, filed Sep. 14, 2001, and entitled Method and Apparatus For Assembling Refastenable Absorbent Garments, U.S. patent application Ser. No. 09/954,480, filed Sep. 14, 2001 and entitled Method and Apparatus For Assembling Refastenable Absorbent Garments, U.S. patent application Ser. No. 09/834,870, filed Apr. 13, 2001, and entitled "Multiple Component Web," U.S. patent application Ser. No. 09/834,875, filed Apr. 13, 2001 and entitled "Method of Assembling Personal Care Absorbent Article," U.S. patent application Ser. No. 09/834,869, filed Apr. 13, 2001, and entitled "Pant-Type Personal Care Articles, and Methods of Making and Using Such Personal Care Articles," U.S. patent application Ser. No. 09/834,787, filed Apr. 13, 2001 and entitled "Methods of Changing Size of Pant-Type Personal Care Articles Outputted from a Manufacturing Process," U.S. patent application Ser. No. 09/834,682, filed Apr. 13, 2001 and entitled "Passive Bonds For Personal Care Article," and U.S. patent application Ser. No. 60/303,307, filed Jul. 5, 2001, and entitled "Refastenable Absorbent Garment," the entire disclosures of which are hereby incorporated by reference.

After the fastener members 42 are applied, the web 100 and fastener members 42 can be further acted upon, for example, by bonding the fastener members 42 to the web 100, preferably with an ultrasonic bonder 194, and are thereafter passed through the second weakening apparatus 104. The second weakening apparatus 104 further weakens the lines of weakness 37 as explained above. In particular, the second weakening apparatus is indexed such that the insert members 126, and in particular the insert portions 130 thereof, are received in the recess 132 at the nip 118 as the line of weakness 37 passes through the nip 118. In one preferred embodiment, the insert portions 130 are spaced along the insert member 126 in the cross direction so as to engage the line of weakness between and on opposite sides of the tab members 53 so as to not to interfere with the tab members as they cross or bridge the lines of weakness 37. Also in the preferred embodiment, the knife 168 positioned between the insert members cuts body panel between adjacent fastener members to form a discrete absorbent garment. Alternatively, where the fastener member bridges two absorbent garments, the knife can also be configured to cut the fastener member to form two discrete fastener members, each joined to a discrete absorbent garment.

In one preferred embodiment, shown in FIG. 14, the front body panel web 100 is bonded to a rear body panel web 196 at side seams, wherein the rear body panel web is positioned over the front body panel web by folding a crotch portion joining or bridging between the body panel webs prior to the web being introduced to the second weakening apparatus 104, including its knife 168. In this embodiment, both the front and rear body panel webs 100, 196 pass through the nip 118, with the front body panel web 100 facing the first roll 114 and the second body panel web 196 facing the second roll. The insert members 126 weaken the lines of weakness 37 in the web 100 without puncturing the web 196.

Article of Manufacture:

Referring to FIGS. 15 and 16, one preferred embodiment of an absorbent garment 2 includes a first, front body panel 4 and a second, rear body panel 6. The term "body panel" refers to the portion(s) of the absorbent garment, whether made of one or more layers or substrates or of one or more pieces or components, that is/are fitted circumferentially around at least the waist region of the user, including for example the user's lower back, buttock, hips and abdomen. Therefore, for example, the body panels can be made of separate discrete members, or they can form part of a one-piece body chassis that further includes a crotch portion.

The first and second body panels each have an inner, bodyside surface 10 and an outer, garment side surface 12. The first, front body panel 4 has a length, which is measured between opposed first and second terminal edges 16 and 20, and which is less than the overall length of the absorbent garment. Likewise, the second, rear body panel 6 has an overall length, which is measured between opposed first and second terminal edges 14 and 18, and which is also less than the overall length of the absorbent garment. Each of the first and second body panels has an outboard edge 24, 28 formed along the outer periphery of laterally opposed side portions of the first and second body panel. It should be understood that the outboard edges of the front and rear body panels can be different lengths.

In one embodiment, shown in FIG. 15, the second body panel includes a tapered edge 26 on each side thereof that forms in part the leg opening, along with the side edges of the absorbent composite 50 and the terminal edge 16 of the first body panel. It should be understood that the first body panel also could be configured with tapered side edges, as shown for example in FIG. 16.

Referring to FIGS. 15 and 16, one or more, and preferably a plurality, meaning two or more, laterally extending elastic elements 36 are secured to each of the first and second body panels. Preferably, a plurality of laterally extending elastic elements are longitudinally spaced across substantially the entire length of the waist portion of the rear body panel 6, although they may be spaced across a lesser length.

In one embodiment, shown in FIG. 15, the front body panel has a "non-elasticized" area 77 wherein there are no laterally extending elastic elements, or other elastic or elastomeric backing members, incorporated therein or making up any portion of the thickness or cross-section of the body panel at that area, which would gather the material. For example elastic elements can extend along the upper waist portion and along the lower terminal edge defining the leg opening. It should be understood, that in an alternative embodiment, one or more separate waist bands, with or without elastic elements, can be secured to one or both of the rear and front body panels, preferably along the upper terminal edges thereof. Similarly, separate leg bands can be secured along the edges of the body panels and absorbent composite that define the leg openings. Alternatively, one or both of the body panels can be formed without any elastic elements.

The various waist and leg elastic elements can be formed from rubber or other elastomeric materials. One suitable material is a LYCRA® elastic material. For example, the various elastic elements can be formed of LYCRA® XA Spandex 540, 740 or 940 detex T-127 or T-128 elastics available from E.I. duPont De Nemours and Company, having an office in Wilmington, Del. Another suitable elastic material is a Kraton® elastic material, available from Shell Oil Co.

Each body panel is preferably formed as a composite, or laminate material, otherwise referred to as substrates or laminates, with the plurality of elastic strands sandwiched therebetween. Preferably two or more layers are bonded with various adhesives, such as hot melt, or by other techniques, including for example and without limitation ultrasonic bonding and heat pressure sealing. In one embodiment, the two layers are made of a nonwoven material. It should be understood that the body panels can be made of a single layer or substrate of nonwoven material, or can be comprised of more than two layers or substrates. Of course, it should be understood that other knitted or woven fabrics, nonwoven fabrics, elastomeric materials, polymer films, laminates and the like can be used to form one or more of the body panel layers. The term "nonwoven" web or material, as used herein, means a web having a structure of individual fibers or filaments that are interlaid, but not in an identifiable manner and without the aid of textile weaving or knitting, as in a knitted or woven fabric.

In one embodiment, the nonwoven layers or substrates can be made by spunbonding. Spunbond nonwoven webs or materials are made from melt-spun filaments or spunbonded fibers which refers to small diameter fibers that are formed by extruding molten thermoplastic material as filaments from a plurality of fine, usually circular capillaries of a spinneret with the diameter of the extruded filaments then being rapidly reduced, for example, by non-eductive or eductive fluid-drawing or other well known spunbonding mechanisms. The production of spunbond nonwoven webs is described in U.S. Pat. No. 4,340,563 to Appel et al., U.S. Pat. No. 3,692,618 to Dorschner et al., U.S. Pat. No. 3,802,817 to Matsuki et al, U.S. Pat. No. 3,502,763 to Hartmann, U.S. Pat. No. 3,276,944 to Levy, U.S. Pat. No. 3,502,538 to Peterson, and U.S. Pat. No. 3,542,615 to Dodo et al, all of which are incorporated herein by reference. The melt-spun filaments formed by the spunbond process are generally continuous and have diameters larger than 7 microns, more particularly, between about 10 and 30 microns. Another frequently used expression of fiber or filament diameter is denier, which is defined as grams per 9000 meters of a fiber or filament. The fibers may also have shapes such as those described in U.S. Pat. No. 5,277,976 to Hogle, et al, U.S. Pat. No. 5,466,410 to Hills and U.S. Pat. Nos. 5,069,970 and 5,057,368 to Largman et al., all of which are incorporated herein by reference. The spunbond filaments usually are deposited, by one or more banks, onto a moving foraminous belt or forming wire where they form a web. Spunbonded filaments generally are not tacky when they are deposited onto the collecting surface.

Spunbond fabrics typically are stabilized or consolidated (pre-bonded) in some manner immediately as they are produced in order to give the web sufficient integrity to withstand the rigors of further processing into a finished product. This stabilization (prebonding) step may be accomplished through the use of an adhesive applied to the filaments as a liquid or powder which may be heat activated, or more commonly, by compaction rolls. As used herein, the term "compaction rolls" means a set of rollers above and below the web used to compact the web as a way of treating a just produced, melt-spun filament, particularly spunbond, web, in order to give the web sufficient integrity for further processing, but not the relatively strong bonding of secondary bonding processes, such as through-air bonding, thermal bonding, ultrasonic bonding and the like. Compaction rolls slightly squeeze the web in order to increase its self-adherence and thereby its integrity.

An alternative means for performing the pre-bonding step employs a hot air knife, as described in U.S. Pat. No. 5,707,468, which is incorporated herein by reference. Briefly, the term "hot air knife" means a process of pre-bonding a just produced melt-spun filament, particularly spunbond, web, in order to impart the web with sufficient integrity, i.e., increase the stiffness of the web, for further processing. A hot air knife is a device that focuses a stream of heated air at a very high flow rate, generally from about 300 to about 3000 meters per minute (m/min.), or more particularly from about 900 to about 1500 m/min., directed at the nonwoven web immediately after its formation. The air temperature usually is in the range of the melting point of at least one of the polymers used in the web, generally between about 90° C. and about 290° C. for the thermoplastic polymers commonly used in spunbonding. The control of air temperature, velocity, pressure, volume and other factors helps avoid damage to the web while increasing its integrity.

The hot air knife's focused stream of air is arranged and directed by at least one slot of about 3 to about 25 millimeters (mm) in width, particularly about 9.4 mm, serving as the exit for the heated air towards the web, with the slot running in a substantially cross-machine direction over substantially the entire width of the web. In other embodiments, there may be a plurality of slots arranged next to each other or separated by a slight gap. The at least one slot usually, but not necessarily, is continuous, and may be comprised of, for example, closely spaced holes. The hot air knife has a plenum to distribute and contain the heated air prior to its exiting the slot. The plenum pressure of the hot air knife usually is between about 2 to about 22 mmHg, and the hot air knife is positioned between about 6.35 mm and about 254 mm, and more particularly from about 19.05 to about 76.20 mm above the forming surface. In a particular embodiment, the hot air knife plenum's cross-sectional area for cross-directional flow (i.e., the plenum cross-sectional area in the machine direction) is at least twice the total slot exit area.

Since the foraminous wire onto which the spunbond polymer is formed generally moves at a high rate of speed, the time of exposure of any particular part of the web to the air discharge from the hot air knife typically is less than a tenth of a second and generally about one hundredth of a second, in contrast with the through-air bonding process, which has a much longer dwell time. The hot air knife process has a great range of variability and control over many factors, including air temperature, velocity, pressure, and volume, slot or hole arrangement, density and size, and the distance separating the hot air knife plenum and the web.

The spunbond process also can be used to form bicomponent spunbond nonwoven webs as, for example, from side-by-side (or sheath/core) linear low density polyethylene/polypropylene spunbond bicomponent filaments. A suitable process for forming such bicomponent spunbond nonwoven webs is described in U.S. Pat. No. 5,418,045 to Pike et al., which is incorporated herein by reference in its entirety.

Commercially available thermoplastic polymeric materials can be advantageously employed in making the fibers or filaments from which pattern-unbonded nonwoven material is formed. As used herein, the term "polymer" shall include, but is not limited to, homopolymers, copolymers, such as, for example, block, graft, random and alternating copolymers, terpolymers, etc., and blends and modifications thereof. Moreover, unless otherwise specially limited, the term "polymer" shall include all possible geometrical configurations of the material, including, without limitation, isotactic, syndiotactic and random symmetries. As used herein, the terms "thermoplastic polymer" or "thermoplastic polymeric material" refer to a long-chain polymer that softens when exposed to heat and returns to its original state when cooled to ambient temperature. Preferably, the spunbond fibers are made of a polypropylene. Other alternative thermoplastic materials include, without limitation, poly (vinyl chloride)s, polyesters, polyamides, polyfluorocarbons, polyolefins, polyurethanes, polystyrenes, polyethylenes, poly(vinyl alcohol)s, caprolactams, and copolymers of the foregoing. The fibers or filaments used in making the nonwoven material may have any suitable morphology and may include hollow or solid, straight or crimped, single component, bicomponent or multicomponent, biconstituent or multiconstituent fibers or filaments, and blends or mixes of such fibers and/or filaments, as are well known in the art.

After the nonwoven web is formed, the pre-bonded or unbonded web is passed through a suitable process or apparatus, including for example a calendar roll, to form a pattern of discrete bonded areas. The term "discrete" as used herein means individual or disconnected, and is contrasted with the term "continuous" as used in U.S. Pat. No. 5,858,515 to Stokes et al, which is hereby incorporated herein by reference, and which describes pattern-unbonded, or point un-bonded nonwoven fabrics having continuous bonded areas defining a plurality of discrete unbonded areas. In one embodiment, the calendar stack (not shown) includes an anvil roll and a pattern roll, which is heated and includes various raised landing portions. The raised portions of the pattern roll thermally bond the fibers to form the bonded areas. The bonds can made of any shape and size. Preferably, the percent bonded area of the web is between about 5% and 25% of the area of the web, and is more preferably between about 10% and 15%. Thereafter, the bonded substrate can be bonded to another substrate with the elastic members disposed therebetween.

In one alternative preferred embodiment, a landing material, which releasably engages the fastener members, can be secured to the body panel. One exemplary landing material is made of the point-unbonded nonwoven material, for example, a 2.0 osy point-unbonded material. One exemplary material of this type has been used in a HUGGIES® Ultratrim Disposable Diaper, which is commercially available from Kimberly-Clark Corporation. In another preferred embodiment, the landing material, which can be comprised of a portion of one of the body panel substrates, e.g., a body panel liner, is made of a nonwoven material, for example, a spunbond material having a basis weight of preferably about 0.6 osy. In other preferred embodiments, the basis weight of each substrate can be between at least about 0.3 and about 2.0 osy, and preferably between about 0.5 osy and about 1.5 osy, and more preferably between about 0.5 osy and about 1.0 osy. Even with a relatively low percent area bonding, the relatively low basis weight nonwoven material exhibits strength and tear characteristics allowing it to be used as a body panel. Other materials that may be used as the nonwoven material include various meltblown materials, and also bonded-carded materials.

In other alternative embodiments, the landing material can be made of a loop material, which typically includes a backing structure and a plurality of loop members extending upwardly therefrom. The loop material can be formed from any suitable material, such as acrylic, nylon or polyester, and can be formed by such methods as warp knitting, stitch bonding or needle punching. Suitable loop materials are available from Guilford Mills, Inc., Greensboro, N.C., U.S.A. under the trade designation No. 36549.

The body panel 4, 6 nonwoven material is preferably substantially hydrophobic, which may optionally be treated with a surfactant or otherwise process to impart a desired level of wettability and hydrophilicity. In one particular embodiment of the invention, the body panel is a nonwoven, wire-weave spunbond polypropylene fabric composed of about 1.6 denier fibers formed into a web having a basis weight of about 0.6 osy. One suitable nonwoven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIGS. 15 and 16, fastening members 42 are preferably attached to the garment side surface of the front body panel and extend laterally inboard relative to the outboard side edge 24 of the front body panel 4 from an attachment location 45. Opposite longitudinally extending lines of weakness 37 separate a middle portion 33 from the opposite side portions 35, such that the side portions 35 are initially breakably attached to opposite sides of the middle portion 33. As explained above, the lines of weakness 37 can comprise a perforation or other series of cuts, a thinning, breakage or separation of material, or a strip of a different kind of material bridging between the middle portion and the side portions that is more easily torn or broken than the material of the middle portion and side portions, which allow a user or the manufacturer to separate the side portions from the middle portion. For example, the absorbent garment can be broken after the garment is applied to a user, or beforehand. Preferably, any fastener members that bridge the line of weakness are first disengaged from the body panel prior to any tearing or breaking of the line of weakness. Preferably, as also explained above, with respect to absorbent garment body panels, it is generally desired to maintain a mean tensile strength across the line of weakness of between about 0 kg to about 6.30 kg (61.8 N or 13.9 lbf), or less than about 14 lbf, for the end user, more preferably less than about 31.11 N or 7 lbf, preferably between about 0 kg and about 3.00 kg (29.43 N or 6.62 lbf), or alternatively preferably less than about 22.25 N or 5 lbf, or alternatively preferably less than about 1.36 kg (13.35 N or 3 lbf), wherein the tensile strength of the body panels across the line of weakness is determined using the testing protocol described below from a group of at least 20 samples. Likewise, with respect to absorbent garment body panels, it is generally desired to maintain a mean trapezoidal tear strength along the line of weakness of between about 0 kg to about 2.27 kg (22.25 N or 5 lbf), for the end user, and more preferably between about 0 kg and about 1.82 kg (17.84 N or 4 lbf), and more preferably less than about 1.36 kg (13.35 N or 3 lbf), wherein the tear strength of the body panels along the line of weakness is determined using the testing protocol described below from a group of at least 20 samples.

It should be understood that the aforementioned mean tensile and tear strength values are preferably calculated according to the testing protocol set forth below. However, it should be understood that the particular type of body panel material, or the fact that it has one or more elastic elements integrated therein, is not important, so long as the body panel has the preferred tensile and tear strengths across and along the line of weakness as described herein. Moreover, it should be understood that the mean tensile and tear strength values for a body panel taken along its entire length that fall within these ranges would also be encompassed within the scope of the invention, regardless of the sample size, i.e., whether smaller or larger. Accordingly, where the body panel is not dimensioned to allow for a sample to be taken according to the procedure set forth below, the tear and tensile strength values can be determined for the entire length of the body panel along and across the line of weakness and thereafter compared with the preferred values set forth herein.

Preferably, the fastening members 42 are secured to the garment-side surface 12 of the side portions 35 between the side edge 24 of the front body panel and the line of weakness 37. It should be understood that, in other embodiments, the fastening members can be secured to the rear body panel and engage the front body panel or, conversely, can be secured to the front body panel and engage the rear body panel. For example, in one preferred embodiment, the fastening members can be secured to the rear body panel and can include a portion crossing over a line of weakness formed along the front body panel, or alternatively along the rear body panel, and can refastenably engage a portion of the front body panel on the other side of the line of weakness. It should be understood that the line of weakness could be formed at the side seam separating the front and rear body panels. Preferably, the fastening members are fixedly secured to the outer, garment-side surface of the front and/or rear body panels, and releasably engage the outer, garment-side surface of the front and/or rear body panels, although it should be understood that the fastening members could be fixedly secured to an inner, body-side surface of front and/or rear body panels and releasably engage an inner, body-side surface of the front and/or rear body panels.

Referring to the preferred embodiments of FIG. 15 and 16, the middle portion 33 preferably does not include a separate landing member secured thereto. Instead, the front body panel itself serves as a landing material. However, a landing member can be secured to the middle portion for releasably engaging the fastener members.

Preferably, the opposite side edges 24 of the front body panel 4 are joined to the opposite side edges 28 of the rear body panel 6 to form a seam 39. The seam 39 is formed by bonding, sewing or otherwise attaching the side edges. For example, in one preferred embodiment, the side seams are formed by ultrasonic bonds. In this way, prior to the breaking of the line of weakness 37, the absorbent garment can be configured as a pant-like garment, which can be pulled over the legs of the user. After the garment is applied to the user, the lines of weakness can be broken, if desired, or left intact, as the fasteners are adjusted to fit the garment to the user. If desired, the lines of weakness can be broken prior to securing the garment to the user, for example when the user is bed-ridden. In this configuration, the garment is laid beneath the user and is secured to the user with the fastening tabs. By providing the side portions, and by connecting the fastening tabs to the front body panel, instead of the rear body panel, the tabs are located at the front of the user so as to not provide discomfort to the user when lying on their backs and to allow the fasteners to be more easily seen and adjusted by the user or caretaker.

It should be understood that the lines of weaknesses and the fasteners can be moved laterally inboard and outboard to provide more or less adjustment capability. It should be understood that the front and rear body panels can be made as an integral unitary member that extends along the crotch from the front to back and with the sides thereof connected to form side seams. Alternatively, the front and rear body panels can be formed integrally as a ring-like member, for example as one body panel extending around the waist and hips of the user, that is attached to a crotch portion that forms leg openings.

In one alternative embodiment, an outer cover is disposed over the entire garment and forms the outer garment side layer or substrate of the front and rear body panels, with the various elastic elements 36, 38 disposed between a bodyside liner on each of the front and rear body panels, which liner preferably is configured as a single substrate, and the outer cover, which is also preferably configured as single substrate. In this way, the portion of the outer cover that overlies the front body panel liner and is fitted around the front of the user forms part of the front body panel, while the portion of the outer cover that overlies the rear body panel liner and is fitted around the rear of the user forms part of the rear body panel. The front and rear body panels, with the liners and with the outer cover forming portions thereof and preferably extending therebetween, forms a chassis. The outer cover is preferably made of a nonwoven material, similar to that of the other body panel materials described herein. It should be understood that the body panels, including the outer cover, can be configured with any number of a plurality of substrates, and that the body panels can include other layers and substrates.

Preferably, as shown in FIGS. 15 and 16, the fastening members 42 comprise a carrier member 43 that is formed in a generally side-ways, "U" shape, with a vertical extending base member 55 and a pair of laterally extending and longitudinally spaced tab members 47, which cross the line of weakness. The carrier member can include a single tab member, or more than two tab members. The carrier members are preferably fixedly secured to the side portions of the front body panel 4 with adhesive bonds 49, sonic bonds, thermal bonds, pinning, stitching or other known types of attachment. In alternative embodiments, the fastening members can be fixedly secured to the rear body panel, or to one or both of the front and rear body panels, e.g., at the seam.

In a preferred embodiment, the pair of fastener members 42 used to releasably secure the front and rear body panels define a "fastening system," which refers to the grouping of fastener members used to releasably secure two or more portions of an absorbent garment. Although the fastening system is shown as being configured with two fastener members, it should be understood that it could include additional fastener members, and that the two-fastener member fastening system shown in the Figures is meant to be illustrative rather than limiting. For example, the fastening system could include three, four or even more fastener members.

Referring to FIG. 14, the fastener members 42, and in particular the carrier members 43, are fixedly connected to the rear body panel base web 196, and after separation, the rear body panel. The tab members 47 can be oriented toward each other on either of the front and rear body panels, or away from each other.

Each carrier member 43 has a longitudinal length and each of the tab members 47 comprises a refastenable portion 51 or an engagement portion having a longitudinal length. The refastenable portion 51 preferably comprises an array of hooks, as explained below, but alternatively can comprise various adhesives, such as pressure sensitive adhesives, buttons, zippers, snaps and other releasable and reattachable fastening devices known to those skilled in the art.

In one preferred embodiment, the refastenable portion 51 comprises a hook-type fastener member, or hook strip, which is secured to the carrier member 43 with adhesive, ultrasonic bonding, stitching or other known attachment devices. The end portion 53 or tip of the carrier member can be left uncovered by the refastenable portion 51, such that it can be lifted or flexed and grasped by a user as they disengage or peel back the fastener member. It should be understood that the term "hook" as used herein means any element capable of engaging another element, and is not intended to limit the form of the engaging elements, for example to include only "hooks," but rather encompasses any form or shape of engaging element, whether unidirectional or bidirectional. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of hook fasteners are the various CS600 hook fasteners, including the XKH-01-002 CS600, 2300 Pin Density hook fastener (Part No. XKH-01-002/60MM/SP#2628), manufactured by Minnesota Mining and Manufacturing Co., St. Paul Minn. Other examples of hook fastener are the Velcro® HTH-851 and HTH-829 hook fasteners available from Velcro USA, Inc.

In one preferred embodiment, a mushroom-type hook strip comprises a homogeneous backing of thermoplastic resin and, integral with backing, an array of upstanding stems distributed across at least one face of the backing, each having a mushroom head. The array of hooks on each strip comprises an engagement portion having a longitudinal length. The stems can have a molecular orientation as evidenced by a birefringence value of at least 0.001, with the mushroom heads having circular disc shapes with generally planar end surfaces opposite the backing, which disc shaped heads preferably have diameter to thickness ratios of greater than about 1.5 to 1.

The stems of the hook strip can be molecularly orientated as evidenced by a birefringence value of at least 0.001. As such, they have significantly greater stiffness and durability, as well as greater tensile and flexural strength, than would be achievable without such orientation. Because of these qualities, the portions of the stems not heated by a heating surface during the forming process remain resiliently flexible during a deforming step, which preferably involves the application of heat to the stem tips by contact with the heated surface of a metal roller. Such contact forms the tip of each stem into a circular disc shaped mushroom head at the tip of each stem, which head has a substantially flat inner surface that enhances its holding power when engaged with a landing material.

As compared to hook strips that have unoriented stems, the enhanced strength of the hooks of the hook strip makes them less likely to break during disengagement. When the hook strip is used with the nonwoven material herein described, the enhanced strength of the hooks makes them less likely to break under disengagement forces than the fibers of the material, a beneficial attribute for at least two reasons. First, broken hooks can create debris whereas a broken fiber typically does not. Second, the nonwoven material typically contains many more engageable fibers than there are hooks per unit area, thus allowing a greater number of disengagements before a hook fastener becomes useless.

Although the stems of the hook strip preferably are generally circular in cross section, other suitable cross sections include rectangular and hexagonal. The stems preferably have fillets at their bases, both to enhance strength and stiffness and for easy release from a mold in which they are formed. In addition, the stems can be tapered, preferably from a larger to a smaller cross-section as one moves from the base to the head.

The stem portions are preferably at an angle of about 90 degrees from the backing substrate, however, this angle can range from about 80 to about 100 degrees, preferably 85 to about 95 degrees. The hook head portion is formed on the distal end of the stem. The hook head can be elongated in one or more directions forming the fiber engaging portions. These fiber engaging portions extend outwardly from the stem portion at any angle so that they can project upwardly away from the film backing, parallel with the film backing or even downward toward the film backing.

For example, the hook head portion has a deformed fiber engaging portion that projects downward. Preferably, the lower surface of the fiber engaging portion also projects downward forming a crook between the lower face of the fiber engaging portion and the stem base portion. In one preferred embodiment, the heads of the hooks generally project at a downward angle from the hook head top portions toward the base. This downward angle (measured from a reference line taken from the top of the hook head and parallel with the backing) is generally from about 0 to about 70 degrees, preferably from about 5 to about 60 degrees and most preferably from about 5 to about 35 degrees (defined by a linear extent running from a center region of the hook head top portion to an end of the hook head fiber engaging portion).

The head shape with its high diameter to thickness ratio, and the small size and close spacing or high density of individual hooks that are provided by the hook strip makes it easier to firmly releasably engage nonwoven materials in shear, possibly because the many thin heads can easily move radially into engagement with rather small fibers. Thus the hook strip is particularly useful for hook-and-loop fastening when the "loops" are provided by nonwoven materials which are not particularly adapted for use as the loop portions of hook and loop fasteners, and which are not as well engaged by known prior art hook strips. For example, the hook strip is particularly well-suited for engaging the topographically flatter nonwoven materials described above, including the nonwoven spunbond material, which has relatively fewer loose, outwardly extending, free fibers than conventional loop materials, but still provides a relatively high number of pores, of sufficient size, such that the material can be engaged by the hooks. Indeed, once the hooks are received in the pores, or embedded in the nonwoven material, the fastening tabs provide excellent shear characteristics, such that the garment is securely fastened during normal wearing conditions.

In general, the hooks are of uniform height, preferably of from about 0.10 to 1.30 mm in height, and more preferably from about 0.18 to 0.51 mm in height; have a density on the backing preferably of from 60 to 1,600 hooks per square centimeter, and more preferably from 125 to 690 hooks per square centimeter, and preferably greater than about 150 hooks per square centimeter; have a stem diameter adjacent the heads of the hooks preferably of from 0.07 to 0.7 mm, and more preferably from about 0.1 to 0.3 mm. The deformed hook heads project radially past the stems on at least one side preferably by an average of about 0.01 to 0.3 mm, and more preferably by an average of about 0.02 to 0.25 mm and have average thicknesses between their outer and inner surfaces (i.e., measured in a direction parallel to the axis of the stems) preferably of from about 0.01 to 0.3 mm and more preferably of from about 0.02 mm to 0.1 mm. The hook heads have average head diameter (i.e., measured radially of the axis of the heads and stems) to average head thickness ratios preferably of from 1.5:1 to 12:1, and more preferably from 2.5:1 to 6:1.

For most uses, the hooks of the hook strip should be distributed substantially uniformly over the entire area of the hook strip, usually in a square or hexagonal array.

To have both good flexibility and strength, the backing of the hook strip preferably is from 0.02 to 0.5 mm thick, and more preferably is from 0.06 to 0.3 mm in thick, especially when the hook strip is made of polypropylene or a copolymer of polypropylene and polyethylene. For some uses, a stiffer backing could be used, or the backing can be coated with a layer of pressure sensitive adhesive on its surfaces opposite the hooks by which the backing could be adhered to a substrate, such as the carrier member 43, so that the backing could then rely on the strength of the substrate to help anchor the hooks.

Virtually any orientable thermoplastic resin that is suitable for extrusion molding may be used to produce the hook strip. Thermoplastic resins that can be extrusion molded and should be useful include polyesters such as poly(ethylene terephthalate), polyamides such as nylon, poly(styrene-acrylonitrile), poly(acrylonitrile-butadiene-styrene), polyolefins such as polypropylene, and plasticized polyvinyl chloride. One preferred thermoplastic resin is a random copolymer of polypropylene and polyethylene containing 17.5% polyethylene and having a melt flow index of 30, that is available as SRD7-463 from Shell Oil Company, Houston, Tex.

The hook strip has preferably substantially continuous planar backing of thermoplastic resin. Integral with the backing is the array of hooks projecting generally at right angles to one major surface of the backing. Each of the hooks has a stem, and, at the end of the stem opposite the backing, a generally circular plate-like cap or head projecting radially past or overhanging the stem so as to form a fiber engaging portion that projects downward. Preferably, the lower surface of the fiber engaging portion also projects downward forming a crook between the lower face of the fiber engaging portion and the stem base portion. The stem can also have a fillet around its base.

When the absorbent garment is secured to the user, the fastening members 42 secured to the side portions of the front body panels 4, or elsewhere as described above, releasably engage or are otherwise connected to the landing member secured to the middle portion of the front body panel 4. In particular, the heads on the hooks engage the fibers of the body panel, whether elasticized or not, or alternatively the landing material making up the landing member. The refastenable portions 51 can be initially engaged with the body panel to form a mechanical bond with the body panel or landing member during the manufacturing process so as to help maintain the connection between the side and middle portions.

Referring to FIGS. 15 and 16, the absorbent garment includes an absorbent composite 50 having first and second longitudinally opposed terminal end edges 60, 62. The absorbent composite preferably includes a substantially liquid permeable topsheet, or liner, and a substantially liquid impermeable backsheet, or outer cover. A retention portion 70 is disposed or sandwiched between the topsheet and the backsheet, which are connected. The topsheet, backsheet and other components of the absorbent composite 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term “absorbent composite” refers to any material or assembly capable of absorbing liquids or bodily exudates, and may be comprised of a single material or component, for example a retention portion.

Additional layers, including for example, a surge layer 72, are also preferably incorporated into the absorbent composite. Preferably, the surge layer does not run the entire length of the absorbent composite and is shorter than the retention portion. The topsheet can be indirectly joined to the backsheet by affixing the topsheet to intermediate layers, such as the surge layer or retention portion, which in turn is affixed to the backsheet. The absorbent composite may also include barrier cuffs, or leakage control shields, formed along the opposite longitudinally extending edges of the absorbent composite.

The retention portion 70 is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion 70 has laterally opposed side edges 74 and preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

Referring to FIG. 15, the opposite garment side of the end regions of the absorbent composite, and in particular, the outer, garment side surface of the backsheet, are secured to the bodyside surface of the longitudinally opposed crotch ends of the first and second body panels 4, 6, and in particular the liner portion of those body panels. It should be understood that the absorbent composite can be secured using any of the methods of attachment described above, including for example various adhesives, stitching or other bonding methods. The absorbent composite can be secured to the body panels with any configuration of attachment lines, swirls, patterns, spots, etc., or can be a full and continuous attachment therebetween. In addition, it should be understood that the absorbent composite can be attached to the garment side surface of the body panels.

Testing:

As explained above, it is desirable to maintain a certain range of tensile strength across, and tear strength along, the line of weakness 37 so as to allow the user to easily separate the side portions 35 and attached rear body panel 5 from the middle portion 33 of the front body panel 4 so that the garment can be removed, or custom fitted to the user. This range of tensile and tear strengths can be accomplished either by sufficiently weakening the body panel 4, or web 100, with the first weakening apparatus 102, for example, by using one of the knife configurations shown in FIGS. 10 and 11, or by further weakening the line of weakness at a second location 104, as shown in FIGS. 1 and 2.

For example, various trapezoidal tear and tensile strengths were determined for various samples of the body panel having a line of weakness formed therein by the various knife embodiments described above and as set forth in Table 1. As can be seen from the test results, the tear and tensile strength decreases as the perforation land area or width decreases. All of the webs tested were strong enough for the body panel web to flow through the process without breaking. In particular, webs with lines of weakness formed by four type of knives (embodiments 2, 3, 11 and 13) were tested, with 20 samples (3.0 inches wide) being tested for each knife. For comparison purposes, ten samples of the body panel taken across its entire length (6.37 inches (162 mm)) were also tested using the number 3 knife embodiment. As can be seen in Tables II and III, the tear and tensile strengths increased for the larger sample. However, as explained above, it should be understood that the mean tensile and tear strength values for a body panel taken along its entire length that fall within the preferred ranges would also be encompassed within the scope of the invention, regardless of the sample size. Accordingly, where the body panel is not dimensioned to allow for a sample to be taken according to the procedure set forth below, the tear and tensile strength values can be determined for the entire length thereof and thereafter compared with the preferred values set forth in certain of the following claims.

The tear and tensile strengths of the samples were determined using a modified test method ASTM D 5733-99, which is hereby incorporated herein by reference. The test inputs included a gage length of 25 mm, a test speed of 12.00 inches per minute, a load limit of 22.5 lb (100 N) and a break sensitivity of 95%. The body panel material tested consisted of two layers of 0.60 osy spunbond material with 6 strands of 940 decitex lycra disposed therebetween. Of course, it should be understood that the material and its composition is not important, but rather that the tear and tensile loads fall into the preferred ranges for the user. Accordingly, the following test protocol can also be used to determine tensile and tear values for materials other than nonwoven materials.

The test results are as follows:

TABLE II

TRAPEZOIDAL TEAR STRENGTH

| | Knife 4 Peak Load Gm | Knife 12 Peak Load Gm | Knife 4 Peak Load Gm | Knife 14 Peak Load Gm | Knife 3 Peak Load Gm |
|---|---|---|---|---|---|
| | 4382.89 | 784.04 | 1084.43 | 2154.94 | 909.30 |
| | 7324.95 | 1417.30 | 1365.10 | 1076.31 | 1895.14 |
| | 3169.81 | 946.41 | 1137.78 | 1616.78 | 1723.49 |

TABLE II-continued

TRAPEZOIDAL TEAR STRENGTH

| | Knife 4 Peak Load Gm | Knife 12 Peak Load Gm | Knife 4 Peak Load Gm | Knife 14 Peak Load Gm | Knife 3 Peak Load Gm |
|---|---|---|---|---|---|
| | 883.08 | 1020.64 | 1135.46 | 7951.70 | 832.75 |
| | 1385.05 | 872.18 | 1536.76 | 5028.96 | 1173.73 |
| | 3248.82 | 1343.07 | 1388.30 | 2361.39 | 1588.95 |
| | 1278.15 | 1185.33 | 1406.86 | 2055.19 | 821.15 |
| | 1947.43 | 883.78 | 1047.31 | 1697.97 | 888.42 |
| | 1171.25 | 1707.25 | 1945.01 | 1619.10 | 1704.93 |
| | 1633.71 | 888.42 | 1910.22 | 2131.74 | 1906.74 |
| | 987.66 | 1612.14 | 803.75 | 1442.81 | 1672.45 |
| | | 2328.91 | 1812.79 | 2760.36 | 1391.78 |
| | | 1558.79 | 1467.17 | 1890.50 | 953.37 |
| | | 1742.04 | 1086.75 | 2277.88 | 670.37 |
| | | 1519.36 | 847.83 | 1946.17 | 1540.24 |
| | | 1482.24 | 1856.87 | 2421.70 | 1087.91 |
| | | 1018.32 | 2130.58 | 1433.53 | 1554.15 |
| | | 869.86 | 932.49 | 2959.85 | 1456.73 |
| | | 1449.77 | 951.05 | 2066.79 | 1421.93 |
| | | 1544.87 | 930.17 | 1744.36 | 6054.24 |
| Mean (gm) | 2492.07 | 1308.74 | 1338.83 | 2431.90 | 1562.39 |
| (Force N/lbf) | 24.42/5.42 | 12.82/2.88 | 13.12/2.95 | 23.83/5.36 | 15.31/3.44 |
| Min (gm) | 883.08 | 784.04 | 803.75 | 1076.31 | 670.37 |
| Max (gm) | 7324.95 | 2328.91 | 2130.58 | 7951.70 | 6054.24 |
| Stdv | 1956.86 | 399.64 | 409.24 | 1534.66 | 1124.63 |

TABLE III

TENSILE STRENGTH

| | Knife 4 Peak Load Gm | Knife 12 Peak Load Gm | Knife 4 Peak Load Gm | Knife 14 Peak Load Gm | Knife 3 Peak Load Gm |
|---|---|---|---|---|---|
| | 7261.04 | 3298.52 | 1867.30 | 4064.00 | 4523.28 |
| | 4328.27 | 2124.78 | 2192.05 | 4648.54 | 3377.38 |
| | 2720.13 | 3293.88 | 3692.85 | 6017.12 | 3535.12 |
| | 7456.25 | 1795.40 | 1549.51 | 2848.51 | 1535.60 |
| | 4923.19 | 3572.23 | 1936.89 | 6355.79 | 3395.94 |
| | 4253.91 | 1697.97 | 3112.95 | 3052.64 | 3001.60 |
| | 4444.47 | 2853.15 | 1584.31 | 3948.01 | 1637.66 |
| | 4588.55 | 2243.08 | 1941.53 | 3201.09 | 2412.42 |
| | 3988.98 | 2556.23 | 1649.26 | 3920.18 | 2166.54 |
| | 4453.77 | 3442.33 | 1735.08 | 4657.82 | 3015.52 |
| | 5076.57 | 1491.52 | 1472.97 | 3646.46 | 1974.01 |
| | | 3256.76 | 2667.58 | 4704.21 | 1802.35 |
| | | 2945.93 | 1871.94 | 5052.16 | 1340.75 |
| | | 2282.52 | 1667.82 | 2257.00 | 1786.12 |
| | | 3813.47 | 2052.87 | 4490.81 | 2356.75 |
| | | 2043.60 | 2477.37 | 4486.17 | 1308.27 |
| | | 2192.05 | 2434.45 | 5636.71 | 4198.53 |
| | | 1229.40 | 1462.53 | 4346.99 | 2038.96 |
| | | 2505.20 | 1636.50 | 3159.34 | 1319.87 |
| | | 2212.93 | 1810.47 | 2417.06 | 1556.47 |
| Mean (gm) | 4863.20 | 2542.55 | 2040.81 | 4145.53 | 2414.16 |
| (Force N/lbf) | 47.66/10.71 | 24.92/5.60 | 20.00/4.50 | 40.63/9.1 | 23.66/5.32 |
| Min (gm) | 2720.13 | 1229.40 | 1462.53 | 2257.00 | 1308.27 |
| Max (gm) | 7456.25 | 3813.47 | 3692.85 | 6355.79 | 4523.28 |
| Stdv | 1376.79 | 736.45 | 581.67 | 1128.06 | 982.43 |

The Trapezoid and Tensile tests were conducted using a modified ASTM D5733-99 "Standard Test Method for Tearing Strength of Nonwoven Fabrics by the Trapezoid Procedure." The test samples were prepared as explained below. No conditioning of the samples was performed or is required. For the tensile testing, the sample was placed in the grips parallel to the perforation line in order to get tensile strengths. All other test settings remained the same as the ASTM D5733-99 test method states.

Trapezoid Test

Sample Preparation & Settings:

Cut a non-stretched 6.0 inch (152.4 mm) wide section from an absorbent garment body panel centered about the line of weakness. The sample may include portions of the front and rear body panel, if those members are joined, for example by a seam.

Cut any fastener members bridging the line of weakness from the body panel sample, thereby exposing the line of weakness.

Stretch the panel across a template or cutting surface that has tape or Velcro hook to keep the sample in place during cutting and marking. Be sure to anchor the panel along both edges of the line of weakness to keep the line of weakness from pulling apart when stretching the panel flat. Then stretch the remaining portion of the panel until it is flat. (It is essential that you are careful not to pull the perforation apart).

Using a template cut the samples to 3.0 inches (76.2 mm) long starting from the front waist edge. In one exemplary embodiment, the sample has 6 waist elastics (approx. 1.36 inches (35 mm)) along the top waist edge of the sample and a non-elastic section (approx. 1.64 inches (41 mm)) along the bottom edge. Of course, it should be understood that the panel may not include any elastic members, or may have elastic members spaced across the entire length.

Figure 17:
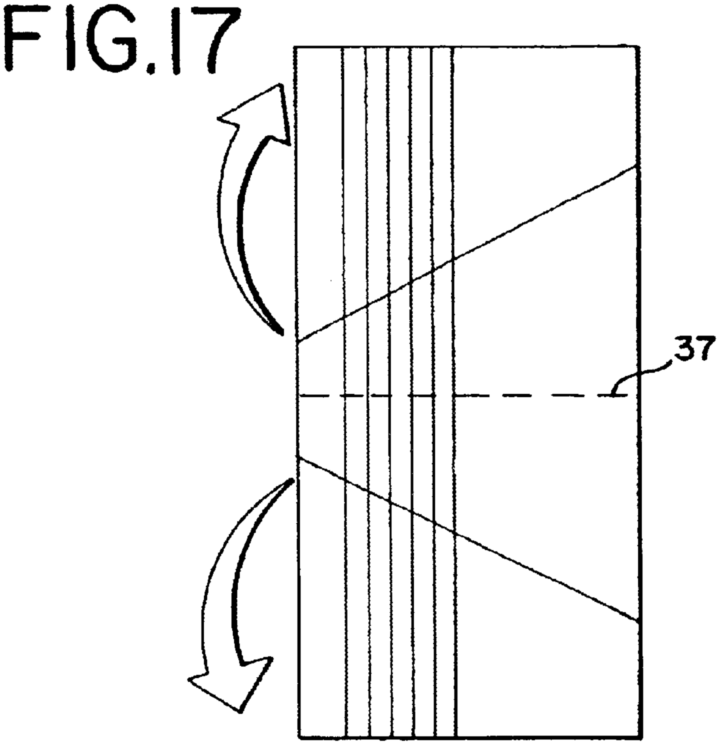
FIG. 17 is an illustration of the sample for a trapezoid test.

Mark the sample with angled lines starting at the front waist edge. The marks should start at 0.5 inches (12.7 mm) on each side of the line of weakness on the waist edge and end up at 2.0 inches (50.8 mm) on each side of the line of weakness on the back edge or non-elastic portion of the sample. It is best to use a template for marking the sample with the angled lines. Mark the template with the line of weakness so that the line of weakness can be lined up in the proper position prior to making the lines on the sample. These lines are used to designate were the grips should be placed on the sample for testing. The line of weakness should be centered or aligned with the "initial cut" slot in the template. However, no initial cut is made in the specimen. The test sample is illustrated in FIG. 17.

Place the sample in the grips on test apparatus with the grips aligned on the angled lines. One suitable test apparatus is the Sintech 1/S machine available from Sintech, a division of MTS Systems Corp., Research Triangle Park, North Carolina. A suitable load cell is available from the same company under part number 4501008/B. Run the test as specified in ASTM D5733-99.

Tensile Test

Sample Preparation & Settings:

Cut a non-stretched 6.0 inch (152.4 mm) wide section from an absorbent garment body panel centered about the line of weakness. The sample may include portions of the front and rear body panel, if those members are joined, for example by a seam.

Cut any fastener members bridging the line of weakness from the body panel sample, thereby exposing the line of weakness.

Stretch the panel across a template or cutting surface that has tape or Velcro hook to keep the sample in place during cutting and marking. Be sure to anchor the panel along both edges of the line of weakness to keep the lien of weakness from pulling apart when stretching the panel flat. Then stretch the remaining portion of the panel until it is flat. (It is essential that you are careful not to pull the perforation apart).

Using a template cut the samples to 3.0 inches (76.2 mm) long starting from the front waist edge. In one exemplary embodiment, the sample has 6 waist elastics (approx. 1.36 inches (35 mm)) along the top waist edge of the sample and a non-elastic section (approx. 1.64 inches (41 mm)) along the bottom edge. Of course, it should be understood that the panel may not include any elastic members, or may have elastic members spaced across the entire length.

Figure 18:
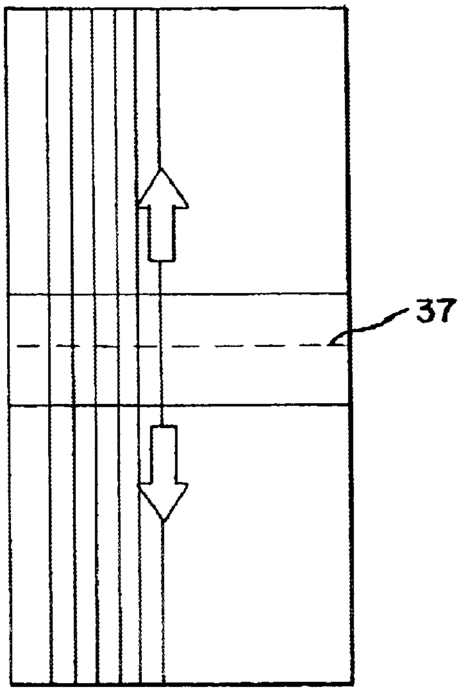
FIG. 18 is an illustration of the sample for a tensile test.

Mark the sample with lines running parallel to the line of weakness. The marks should start at 0.5 inches (12.7 mm) on each side of the line of weakness on the waist edge (elastic edge) and end up at 0.5 inches (12.7 mm) on each side of the line of weakness on the back edge or non-elastic portion of the sample. It is best to use a template for marking the sample with the parallel lines 1 inch (approx. 25 mm) apart. Mark the template with the line of weakness line so that the line of weakness can be lined up in the proper position prior to making the lines on the sample. The sample is illustrated in FIG. 18. These lines are used to designate were the grips should be placed on the sample for testing.

Place the sample in the grips on the testing machine referenced above on the parallel lines and run test with the settings as specified in ASTM D5733-99.

The ASTM D5733-99 test method specifies that the apparatus is a Tensile Testing Machine, of the constant-rate-of-extension (CRE) type conforming to the requirements of Specification D 76 with authographic recorder, or automatic microprocessor data gathering systems. One suitable machine is disclosed above. The clamps have all gripping surfaces parallel, flat, and capable of preventing slipping of the specimen during a test, and measure 50 by no less than 75 mm (2 by no less than 3 in.), with the longer dimension perpendicular to the direction of application of the force. The use of hydraulic pneumatic clamping systems with a minimum of 50 by 75-mm (2 by 3-in.) serrated or rubber jaw faces having a clamping force at the grip faces of 13 to 14 kN (2900 to 3111 lbf) is recommended. Manual clamping is permitted providing no slippage of the specimen is observed. For some materials, to prevent slippage when using jaw faces other than serrated, such as rubber-faced jaws, they may be covered with a No. 80 to 120 medium-grit emery cloth. Secure the emery cloth to the jaw faces with pressure sensitive tape.

The cutting die or template has a 3×6 dimension with tolerances of +/−0.5%. A trapezoidal-shaped marking template having dimensions with tolerances of +/−0.5% is shown in ASTM D5733-99.

The ASTM D5733-99 test method specifies the following steps to prepare the apparatus: (1) set the distance between the clamps at the start of the test at 25+/−1 mm (1+/−0.05 in.), (2) select the full-scale force range of the testing machine such that the maximum force occurs between 15 and 85% of full-scale force, (3) set the testing speed to 300+/−10 mm (12+/−0.5 in./min.), and (4) verify calibration of the tensile testing machine as directed to the manufacturer's instructions or Specification D 76. When using microprocessor automatic data gathering systems, set the appropriate parameters as defined in the manufacturer's instructions.

The ASTM D5733-99 test method specifies the following procedure for testing the samples: (1) secure the test specimen in the machine as set forth above, including clamping along the nonparallel sides of the trapezoid for the tear test such that the end edges of the clamps are in line with the 25-mm (1-in.) long side of the trapezoid, and the cut is halfway between the clamps, or clamping along the parallel lines of the sample for the tensile test, and hold the short edge taut and let the remaining fabric lie in folds, (2) start the machine and record the tearing or tensile force on the recording device (the tearing force may increase to a simple maximum value, or may show several maxima and minima), (3) after the crosshead has moved to produce approximately 6 mm (0.25 in.) of fabric tear, record the maximum tearing force, or record the maximum tensile force after the fabric has broken, and (4) stop the crosshead motion after a total clamp separation of approximately 75 mm (3 in.) or the fabric has torn completely across and return the crosshead to its starting position.

If a fabric slips in the jaws or if 25% or more of the specimens break at a point within 5 mm (0.25 in.) of the edge of the jaw, then the jaws may be padded: the fabric may be coated under the jaw face area or the jaw face may be modified. If any of these modifications are used, state the method of modification in the report. If 25% or more of the specimens break at a point within 5 mm (0.25 in.) of the edge of the jaw after making these modifications, the fabric may be considered untearable by this test method.

Calculate the trapezoid tearing force and tensile force for individual specimens using readings directly from the data collection system. Record the maximum tearing and tensile force to the nearest 0.5 N (0.1 lbf). Calculate the average trapezoid tearing along and tensile across the line of weakness for each sample. Run a minimum of 20 samples for each test.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A method for weakening a portion of a web comprising:

moving said web in a machine direction between at least a first location and a second location, wherein said second location is positioned downstream of said first location;

forming a line of weakness in said web at said first location, wherein said web has a first tensile strength across said line of weakness; and weakening said line of weakness at a second location, wherein said web has a second tensile strength across said line of weakness aller said line of weakness is weakened at said second location, wherein said first tensile strength is greater than said second tensile strength, wherein said weakening said line of weakness at said second location comprises separating portions of said web along said line of weakness at said second location.

2. The invention of claim 1 wherein said forming said line of weakness in said web at said first location comprises forming a cross-direction line of weakness in said web.

3. The invention of claim 1 wherein said forming said line of weakness in said web at said first location comprises successively forming a plurality of spaced apart cross-direction lines of weakness in said web, and wherein said weakening said line of weakness at said second location comprises successively weakening said plurality of said spaced apart cross-direction lines of weakness.

4. The invention of claim 1 wherein said forming said line of weakness at said first location comprises perforating said web.

5. The invention of claim 3 wherein said weakening said line of weakness at said second location comprises breaking a portion of said perforated web along said line of weakness.

6. A method for weakening a portion of a web comprising:

moving said web in a machine direction between at least a first location and a second location, wherein said second location is positioned downstream of said first location;

perforating said web along a cross-direction at said first location and thereby forming a cross-direction perforation in said web; and moving said web between first and second moveable members at said second location, wherein said first moveable member comprises at least one insert member and wherein said second moveable member comprises at least one recess shaped to receive said insert member; and pushing at least a portion of said web at said cross-direction perforation with said insert member into said recess.

7. The invention of claim 6 wherein said insert member comprises a bar and wherein said recess comprises a groove.

8. The invention of claim 6 comprising a plurality of insert members spaced apart along said cross-direction in alignment with said cross-direction perforation.

9. The invention of claim 6 wherein said forming said perforation in said web at said first location comprises successively forming a plurality of spaced apart cross-direction perforations in said web, and wherein said pushing said at least said portion of said web at said cross-direction perforation with said insert member into said recess comprises successively pushing at least a portion of said web at said plurality of spaced apart cross-direction perforations into said recess.

10. The invention of claim 6 wherein said first and second moveable members comprise first and second rolls.

11. The invention of claim 6 wherein said second moveable member comprises a roll having an outer circumferential surface, wherein said recess is formed radially inwardly from said outer circumferential surface.

12. The invention of claim 6 wherein said first moveable member comprises a plurality of insert members spaced circumferentially around a perimeter of said first moveable member at a plurality of circumferentially spaced perimeter positions.

13. The invention of claim 12 further comprising a plurality of insert members spaced along said cross-direction at each of plurality of said circumferentially spaced perimeter positions.

14. A method for weakening a portion of a web comprising:

moving said web in a machine direction between at least a first location and a second location, wherein said second location is positioned downstream of said first location;

perforating said web along a cross-direction at said first location and thereby forming a cross-direction perforation in said web; and moving said web between first and second moveable members, wherein said first moveable member comprises at least one insert member and wherein said second moveable member comprises at least one recess shaped to receive said insert member;

pushing at least a portion of said web at said cross-direction perforation with said insert member into said recess; and directing an air supply through said insert member.

15. The invention of claim 14 wherein said insert member comprises a channel for supplying said air supply.

16. A method for weakening a portion of a web comprising:

moving said web in a machine direction between at least a first location and a second location, wherein said second location is positioned downstream of said first location;

forming a line of weakness in said web at said first location, wherein said web has a first tensile strength across said line of weakness; and weakening said line of weakness at a second location, wherein said web has a second tensile strength across said line of weakness after said line of weakness is weakened at said second location, wherein said first tensile strength is greater than said second tensile strength, wherein said weakening said line of weakness at said second location comprises moving said web between a first moveable member and a second member, wherein said first moveable member comprises at least one insert member and wherein said second member comprises at least one recess shaped to receive said insert member, and further comprising pushing at least a portion of said web at said line of weakness with said insert member into said recess.

17. The invention of claim 16 wherein said insert member comprises a bar and wherein said recess comprises a groove.

18. The invention of claim 16 comprising a plurality of spaced apart insert members.

19. The invention of claim 16 wherein said first moveable member and said second member comprise first and second rolls respectively.

20. The invention of claim 19 wherein said second roll has an outer circumferential surface, wherein said recess is formed radially inwardly from said outer circumferential surface.

21. A method for weakening a portion of a web comprising:

moving said web in a machine direction between at least a first location and a second location, wherein said second location is positioned downstream of said first location;

forming a line of weakness in said web at said first location, wherein said web has a first tensile strength across said line of weakness;

weakening said line of weakness at a second location, wherein said web has a second tensile strength across said line of weakness after said line of weakness is weakened at said second location, wherein said first tensile strength is treater than said second tensile strength, wherein said weakening said line of weakness at said second location comprises moving said web between first and second moveable members, wherein said first moveable member comprises at least one insert member and wherein said second moveable member comprises at least one recess shaped to receive said insert member, and further comprising pushing at least a portion of said web at said line of weakness with said insert member into said recess; and directing an air supply through said insert member.

22. The invention of claim 21 wherein said insert member comprises a channel for supplying said air supply.

* * * * *